United States Patent
Saito

(10) Patent No.: US 9,079,843 B2
(45) Date of Patent: Jul. 14, 2015

(54) 23-YNE-VITAMIN $D_3$ DERIVATIVE

(71) Applicant: TEIJIN PHARMA LIMITED, Chiyoda-ku, Tokyo (JP)

(72) Inventor: Hiroshi Saito, Hino (JP)

(73) Assignee: Teijin Pharma Limited, Tokyo (JP)

( * ) Notice: Subject to any disclaimer, the term of this patent is extended or adjusted under 35 U.S.C. 154(b) by 0 days.

(21) Appl. No.: 14/612,781

(22) Filed: Feb. 3, 2015

(65) Prior Publication Data

US 2015/0148552 A1    May 28, 2015

Related U.S. Application Data

(62) Division of application No. 13/880,637, filed as application No. PCT/JP2011/074414 on Oct. 24, 2011, now Pat. No. 9,006,220.

(30) Foreign Application Priority Data

Oct. 25, 2010   (JP) ................................ 2010-238524

(51) Int. Cl.
    *C07F 7/18*         (2006.01)
    *C07C 401/00*     (2006.01)

(52) U.S. Cl.
    CPC ........... *C07C 401/00* (2013.01); *C07C 2101/14* (2013.01); *C07C 2102/24* (2013.01)

(58) Field of Classification Search
    USPC .......................................... 552/653; 556/437
    See application file for complete search history.

(56) References Cited

U.S. PATENT DOCUMENTS

| | | | |
|---|---|---|---|
| 4,804,502 | A | 2/1989 | Baggiolini et al. |
| 5,525,745 | A * | 6/1996 | DeLuca et al. ................ 552/653 |
| 6,410,523 | B1 | 6/2002 | Watanabe |
| 2002/0045772 | A1 | 4/2002 | Watanabe |
| 2002/0094972 | A1 | 7/2002 | Hatakeyama et al. |

FOREIGN PATENT DOCUMENTS

| | | |
|---|---|---|
| EP | 0808832 | 11/1997 |
| EP | 1260502 | 11/2002 |
| JP | 2009013154 | 1/2009 |
| JP | 2009256361 | 11/2009 |
| WO | 92/03414 A1 | 3/1992 |
| WO | 97/46522 A1 | 12/1997 |
| WO | 9903829 | 1/1999 |
| WO | 9952863 | 10/1999 |
| WO | 0162723 | 8/2001 |

OTHER PUBLICATIONS

Communication for EP 11836202.9 dated Oct. 13, 2010, with Supplementary European Search Report (dated Oct. 3, 2013).
International Search Report for PCT/JP2011/074414, filed Nov. 22, 2011.

* cited by examiner

*Primary Examiner* — Sabiha N Qazi
(74) *Attorney, Agent, or Firm* — Sughrue Mion, PLLC

(57) ABSTRACT

To provide a novel vitamin $D_3$ derivative useful as a therapeutic agent for osteoporosis.
Provided is a vitamin $D_3$ derivative represented by the following formula (1) or a medicinally acceptable solvate thereof:

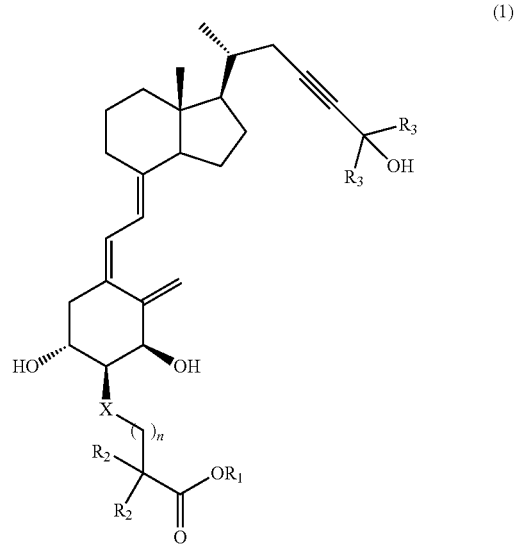

(1)

wherein $R_1$ represents a hydrogen atom, an alkyl group having 1 to 6 carbon atoms, an alkylcarbonyloxyalkyl group with each alkyl having 1 to 6 carbon atoms, or an arylcarbonyloxyalkyl group with the aryl having 6 to 10 carbon atoms and the alkyl having 1 to 6 carbon atoms; $R_2$ represents a hydrogen atom or an alkyl group having 1 to 6 carbon atoms or, together with the other $R_2$ and the carbon atom to which they are bound to, may form a cyclic alkyl group having 3 to 6 carbon atoms; $R_3$ represents an alkyl group having 1 to 6 carbon atoms or, together with the other $R_3$ and the carbon atom to which they are bound to, may form a cyclic alkyl group having 3 to 6 carbon atoms; X represents an oxygen atom or a methylene group; and n represents an integer of 1 or 2.

1 Claim, No Drawings

23-YNE-VITAMIN $D_3$ DERIVATIVE

CROSS REFERENCE TO RELATED APPLICATIONS

This application is a Divisional of U.S. application Ser. No. 13/880,637, filed May 2, 2013 (now allowed); which is a National Stage of International Application No. PCT/JP2011/074414 filed Oct. 24, 2011; which claims priority based on Japanese Patent Application No. 2010-238524 filed Oct. 25, 2010; the contents of all of which are incorporated herein by reference in their entirety.

TECHNICAL FIELD

The present invention relates to a vitamin $D_3$ derivative or a medicinally acceptable solvate thereof which is useful as a drug, to a therapeutic agent using the same, to a pharmaceutical composition comprising the same, and to a production intermediate thereof. More specifically, the present invention relates to a 23-yne-vitamin $D_3$ derivative or a medicinally acceptable solvate thereof, to a pharmaceutical composition comprising the same, to a therapeutic agent comprising the same as an active ingredient for osteoporosis, malignant tumor psoriasis, hyperparathyroidism, inflammatory airway disease, rheumatoid arthritis, diabetes mellitus, hypertension, alopecia, acne, or dermatitis, and to a production intermediate thereof.

BACKGROUND ART

Activated vitamin $D_3$ derivatives regulate bone remodeling, consisting of bone formation and bone resorption, and show bone a density-increasing effect. Thus, they are being used as a valuable therapeutic agent for osteoporosis. However, these active vitamin $D_3$ derivatives, $1\alpha,25$-dihydroxyvitamin $D_3$ for example, do not necessarily show a satisfactory amount of increase in the bone mineral density. When the dose is increased in order to increase the bone mineral density, there occurs an increase in a serum calcium value rather than further increase in the bone mineral density, causing elevation of the serum calcium value by 1 mg/dL or more, a value considered as one of the criteria for clinical undesirability. Thus, there are occasional cases where a sufficient bone mineral density-increasing effect is not obtained (International Publication No. WO 01/62723). Therefore, there is an earnest desire for an activated vitamin $D_3$ derivative which exhibits a strong bone mineral density-increasing effect without increasing the serum calcium value. Heretofore, there have been synthesized a multitude of vitamin $D_3$ derivatives in an effort to obtain such a derivative, but there has not yet been found any derivative which has a satisfactory profile.

SUMMARY OF INVENTION

An object of the present invention is to provide a novel vitamin $D_3$ derivative or a medicinally acceptable solvate thereof which exhibits a desired pharmacological effect isolated from the blood calcium increasing effect.

Further, an object of the present invention is to provide a therapeutic agent for osteoporosis, malignant tumor, psoriasis, hyperparathyroidism, inflammatory airway disease, rheumatoid arthritis, diabetes mellitus, hypertension, alopecia, acne, or dermatitis, comprising the vitamin $D_3$ derivative or a pharmaceutically acceptable solvate thereof as an active ingredient.

Furthermore, an object of the present invention is to provide a pharmaceutical composition comprising the vitamin $D_3$ derivative or an medicinally acceptable solvate thereof.

Still further, an object of the present invention is to provide an intermediate of the vitamin $D_3$ derivative suitable for producing the vitamin $D_3$ derivative or a medicinally acceptable solvate thereof.

The present inventors conducted diligent research in order to solve the above-mentioned problems and, as a result, reached the following invention.

That is, the present invention is a vitamin $D_3$ derivative represented by the following formula (1) or a medicinally acceptable solvate thereof.

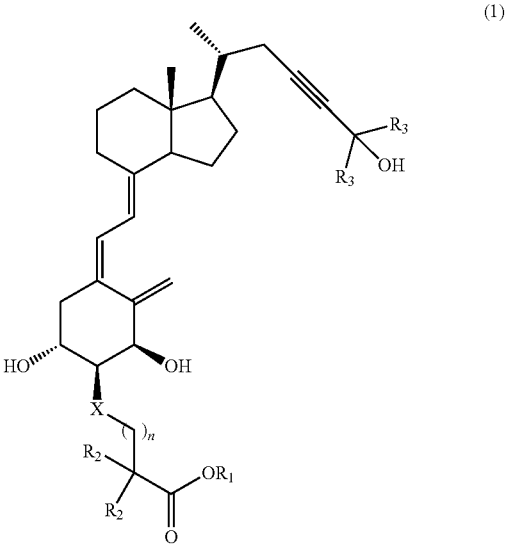

(1)

wherein
$R_1$ represents a hydrogen atom, an alkyl group having 1 to 6 carbon atoms, an alkylcarbonyloxyalkyl group with each alkyl having 1 to 6 carbon atoms, or an arylcarbonyloxyalkyl group with the aryl having 6 to 10 carbon atoms and the alkyl having 1 to 6 carbon atoms; $R_2$ represents a hydrogen atom or an alkyl group having 1 to 6 carbon atoms or, together with the other $R_2$ and the carbon atom to which they are bound to, may form a cyclic alkyl group having 3 to 6 carbon atoms; $R_3$ represents an alkyl group having 1 to 6 carbon atoms or, together with the other $R_3$ and the carbon atom to which they are bound to, may form a cyclic alkyl group having 3 to 6 carbon atoms; X represents an oxygen atom or a methylene group; and n represents an integer of 1 or 2.

Further, the present invention is a pharmaceutical composition comprising the vitamin $D_3$ derivative represented by the above formula (1) or a medicinally acceptable solvate thereof, and a pharmaceutically acceptable carrier.

Furthermore, the present invention is a therapeutic agent for one or more diseases selected from the group consisting of osteoporosis, malignant tumor, psoriasis, hyperparathyroidism, inflammatory airway disease, rheumatoid arthritis, diabetes mellitus, hypertension, alopecia, acne, and dermatitis, comprising the vitamin $D_3$ derivative represented by the above formula (1) or a medicinally acceptable solvate thereof as an active ingredient.

Still further, the present invention is a production intermediate for the vitamin $D_3$ derivative, the intermediate being represented by formula (2):

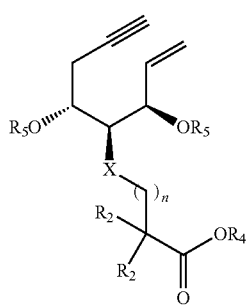

(2)

wherein $R_2$, X, and n are the same as in the above formula (1); $R_4$ represents $R_1$ in the above formula (1), a methoxymethyl group, a methoxyethoxymethyl group, a tetrahydrofuranyl group, a tetrahydropyranyl group, or a benzyloxy methyl group; and $R_5$ represents a protecting group for a hydroxyl group.

According to the present invention, there is provided a novel vitamin $D_3$ derivative or a medicinally acceptable solvate thereof, which is effective for treating various diseases represented by osteoporosis, malignant tumor, psoriasis, hyperparathyroidism, inflammatory airway disease, rheumatoid arthritis, diabetes mellitus, hypertension, alopecia, acne, dermatitis and the like. Further, the production intermediate represented by the above formula (2) of the present invention is useful for producing the vitamin $D_3$ derivative and the like of the present invention.

DESCRIPTION OF EMBODIMENTS

The terms used in the present invention are defined as follows.

The "alkyl group" means a linear, branched, or cyclic aliphatic hydrocarbon group. The alkyl group having 1 to 6 carbon atoms specifically include, for example, a methyl group, an ethyl group, a propyl group, an isopropyl group, a butyl group, an isobutyl group, a t-butyl group, a pentyl group, an isopentyl group, a hexyl group, a cyclopropyl group, a cyclopropylmethyl group, and a cyclohexyl group.

The "alkylcarbonyloxyalkyl group" specifically includes a t-butylcarbonyloxymethyl group.

The "arylcarbonyloxyalkyl group" specifically includes a phenylcarbonyloxymethyl group.

In the above formula (1), $R_1$ represents a hydrogen atom, an alkyl group having 1 to 6 carbon atoms, an alkylcarbonyloxyalkyl group with each alkyl having 1 to 6 carbon atoms, or an arylcarbonyloxyalkyl group with the aryl having 6 to 10 carbon atoms and the alkyl having 1 to 6 carbon atoms. Among these, preferable is a hydrogen atom, a methyl group, an ethyl group, a propyl group, an isopropyl group, or a t-butyl group; and especially preferable is a hydrogen atom or an isopropyl group. As the alkylcarbonyloxyalkyl group, preferable is a t-butylcarbonyloxymethyl group. Further, preferable as the arylcarbonyloxyalkyl group is a phenylcarbonyloxyalkyl group.

In the above formula (1), $R_2$ represents a hydrogen atom or an alkyl group having 1 to 6 carbon atoms or, together with the other $R_2$ and the carbon atom to which they are bound to, may form a cyclic alkyl group having 3 to 6 carbon atoms. Among these, $R_2$ is preferably a hydrogen atom or a methyl group; or when $R_2$, together with the other $R_2$ and the carbon atom to which they are bound, forms a cycloalkyl group, preferable is a cyclopropyl group.

In the above formula (1), $R_3$ represents an alkyl group having 1 to 6 carbon atoms or, together with the other $R_3$ and the carbon atom to which they are bound to, may form a cyclic alkyl group. As the alkyl group having 1 to 6 carbon atoms, preferable are a methyl group and an ethyl group. Further, when $R_3$, together with the other $R_3$ and the carbon atom to which they are bound, forms a cycloalkyl group, preferable is a cyclopentyl group.

Further, in the above formula (1), X represents an oxygen atom or a methylene group.

Furthermore, in the above formula (1), n represents an integer of 1 or 2, where especially preferably n is 1.

As preferred specific examples of the vitamin $D_3$ derivative represented by the formula (1) of the present invention, there may be mentioned the compounds shown in the following table.

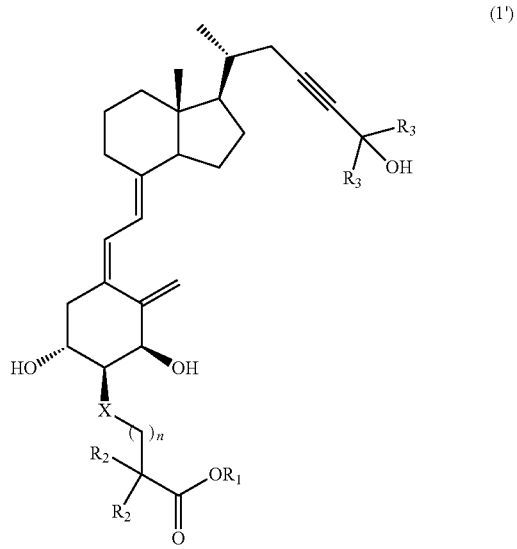

(1')

TABLE 1

| Compound No. | $R_1$ | $R_2$ | $R_3$ | X | n |
|---|---|---|---|---|---|
| C-1 | Hydrogen atom | Hydrogen atom | Methyl group | Oxygen atom | 1 |
| C-2 | Methyl group | Hydrogen atom | Methyl group | Oxygen atom | 1 |
| C-3 | Ethyl group | Hydrogen atom | Methyl group | Oxygen atom | 1 |
| C-4 | Propyl group | Hydrogen atom | Methyl group | Oxygen atom | 1 |
| C-5 | Isopropyl group | Hydrogen atom | Methyl group | Oxygen atom | 1 |
| C-6 | t-Butyl group | Hydrogen atom | Methyl group | Oxygen atom | 1 |
| C-7 | t-Butylcarbonyl-oxymethyl group | Hydrogen atom | Methyl group | Oxygen atom | 1 |
| C-8 | Phenylcarbonyl-oxymethyl group | Hydrogen atom | Methyl group | Oxygen atom | 1 |
| D-1 | Hydrogen atom | Hydrogen atom | Methyl group | Methylene group | 1 |
| D-2 | Methyl group | Hydrogen atom | Methyl group | Methylene group | 1 |
| D-3 | Ethyl group | Hydrogen atom | Methyl group | Methylene group | 1 |
| D-4 | Propyl group | Hydrogen atom | Methyl group | Methylene group | 1 |
| D-5 | Isopropyl group | Hydrogen atom | Methyl group | Methylene group | 1 |
| D-6 | t-Butyl group | Hydrogen atom | Methyl group | Methylene group | 1 |
| E-1 | Hydrogen atom | Cyclopropyl | Methyl group | Oxygen atom | 1 |
| E-2 | Methyl group | Methyl group | Methyl group | Oxygen atom | 1 |
| F-1 | Hydrogen atom | Hydrogen atom | Ethyl group | Oxygen atom | 1 |
| F-2 | Hydrogen atom | Hydrogen atom | Cyclopentyl | Oxygen atom | 1 |

If necessary, the vitamin $D_3$ derivative of the present invention can be converted to a medicinally acceptable solvate.

Such a solvent includes water, methanol, ethanol, 1-propanol, 2-propanol, butanol, t-butanol, acetonitrile, acetone, methyl ethyl ketone, chloroform, ethyl acetate, diethyl ether, t-butyl methyl ether, benzene, toluene, DMF, DMSO, and the like. Especially, there may be mentioned water, methanol, ethanol, 1-propanol, 2-propanol, acetonitrile, acetone, methyl ethyl ketone, and ethyl acetate as preferable solvents.

In addition, $R_5$ in the above formula (2) represents a protecting group for a hydroxyl group. The protecting group for a hydroxyl group includes a methoxymethyl group, an acyl group having 1 to 3 carbon atoms (the number of carbon atoms includes the carbonyl carbon), a trimethylsilyl group, a triethylsilyl group, a t-butyldimethylsilyl group, a t-butyldiphenylsilyl group, and the like. Among these, a triethylsilyl group and t-butyldimethylsilyl group may be mentioned as preferable examples.

Further, $R_4$ in the above formula (2) represents $R_1$ in the above formula (1) or represents a methoxymethyl group, a methoxyethoxymethyl group, a tetrahydrofuranyl group, a tetrahydropyranyl group, or a benzyloxymethyl group. Among these, preferable is a methyl group, an ethyl group, a propyl group, an isopropyl group; or a t-butyl group, a t-butylcarbonyloxymethyl group, a phenylcarbonyloxyalkyl group, or a benzyloxymethyl group.

Furthermore, in the above formula (2), n represents an integer of 1 or 2, wherein n is especially preferably 1.

Synthesis of the vitamin $D_3$ derivative represented by the above formula (1) may be performed by any method but may, for example, be carried out as described in the following Scheme 1. That is, after compound (2) and compound (3) are subjected to a coupling reaction, the protecting group of the hydroxyl group is removed, and, if necessary, the ester group is hydrolyzed to obtain the target material (1).

Scheme 1

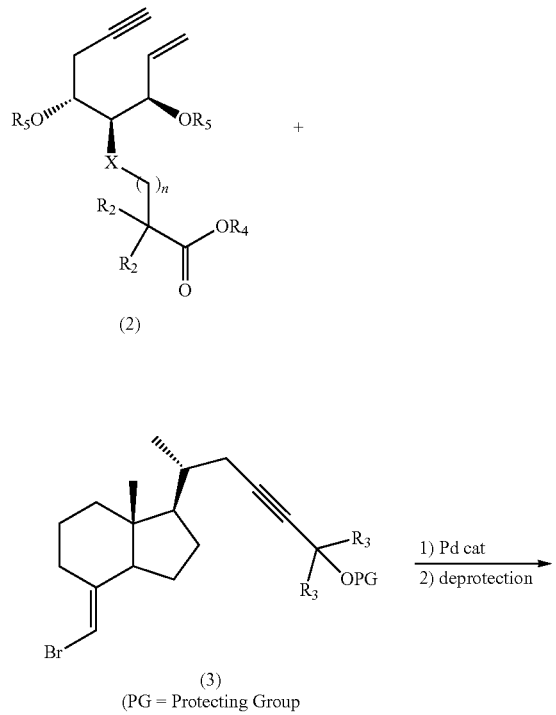

(2)

(3)
(PG = Protecting Group)

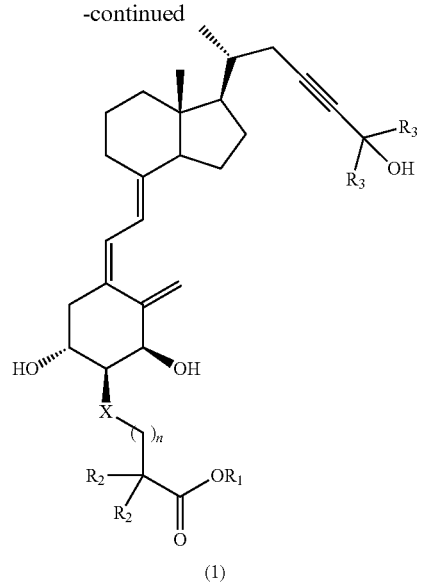

(1)

In the reaction formula above, $R_1$ to $R_5$ in the compound (1) and the compound (2) are the same as in the above formula (1) and formula (2). Further, in the reaction formula above, $R_3$ in the compound (3) are the same as $R_3$ in the above formula (1). Furthermore, OPG in the compound (3) represents a protected hydroxyl group. Specifically, the protecting group includes a trimethylsilyl group, a triethylsilyl group, and a methoxymethyl group.

In the above Scheme 1, when $R_2$ is a hydrogen atom, the compound (2) can be synthesized from an ene-yne compound (4) according to the following Scheme 2, the ene-yne compound (4) being described, for example, in a literature (Takayama, et al., "Vitamin D Analog in Cancer Prevention and Therapy," Recent Results in Cancer Research, Vol. 164, Springer, pp. 289-317, 2003 and the like). That is, by selectively removing the protecting group (t-butyldimethylsilyl group; TBS group) of the primary hydroxyl group of (4), there is obtained compound (5). Then, the hydroxyl group of (5) is oxidized to a carboxyl group, which is subsequently esterified to obtain the desired (2) ($R_2$=TBS).

Scheme 2

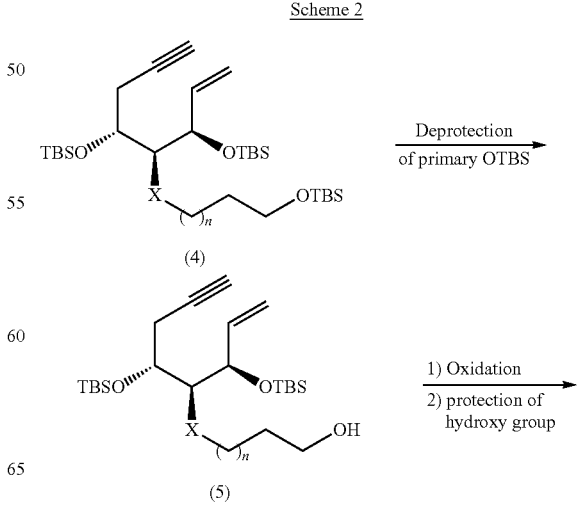

7
-continued

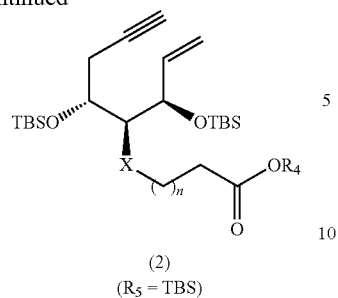

(2)
($R_5$ = TBS)

Meanwhile, in the above Scheme 1, when $R_3$ is a methyl group, compound (3) can be synthesized as described in the following Scheme 3.

That is, the compound (3) can be obtained by bromomethylenation of compound (6), the latter compound being described in a literature (for example, U.S. Pat. No. 4,804,502).

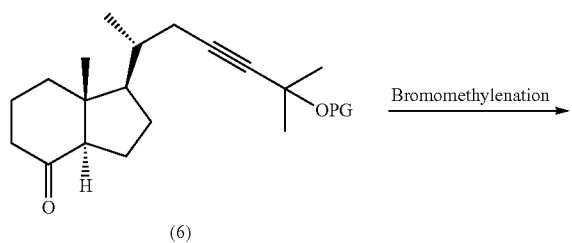

8
-continued

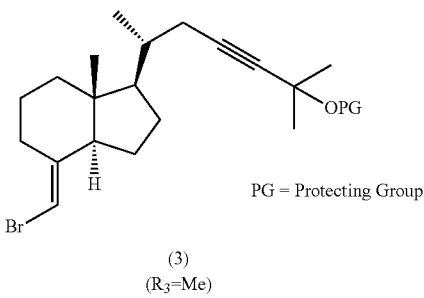

(3)
($R_3$=Me)

Further, among the vitamin $D_3$ derivatives represented by the above formula (1), a compound wherein $R_2$ is a hydrogen atom can also be synthesized according to the method shown in the following Scheme 4 in addition to the above Scheme 1. That is, the compound (5) in Scheme 2 is protected with a pivaloyl group to obtain compound (7), which is subjected to coupling with the compound (3) in Scheme 1 and deprotection of the hydroxyl group at the terminal of a substituent attached to 2-position of the A ring to obtain compound (8). The hydroxyl group of the compound obtained is oxidized to a carboxylic acid and, finally, all protecting groups of the hydroxyl groups are removed to obtain the compound (1) ($R_2$=H).

Scheme 4

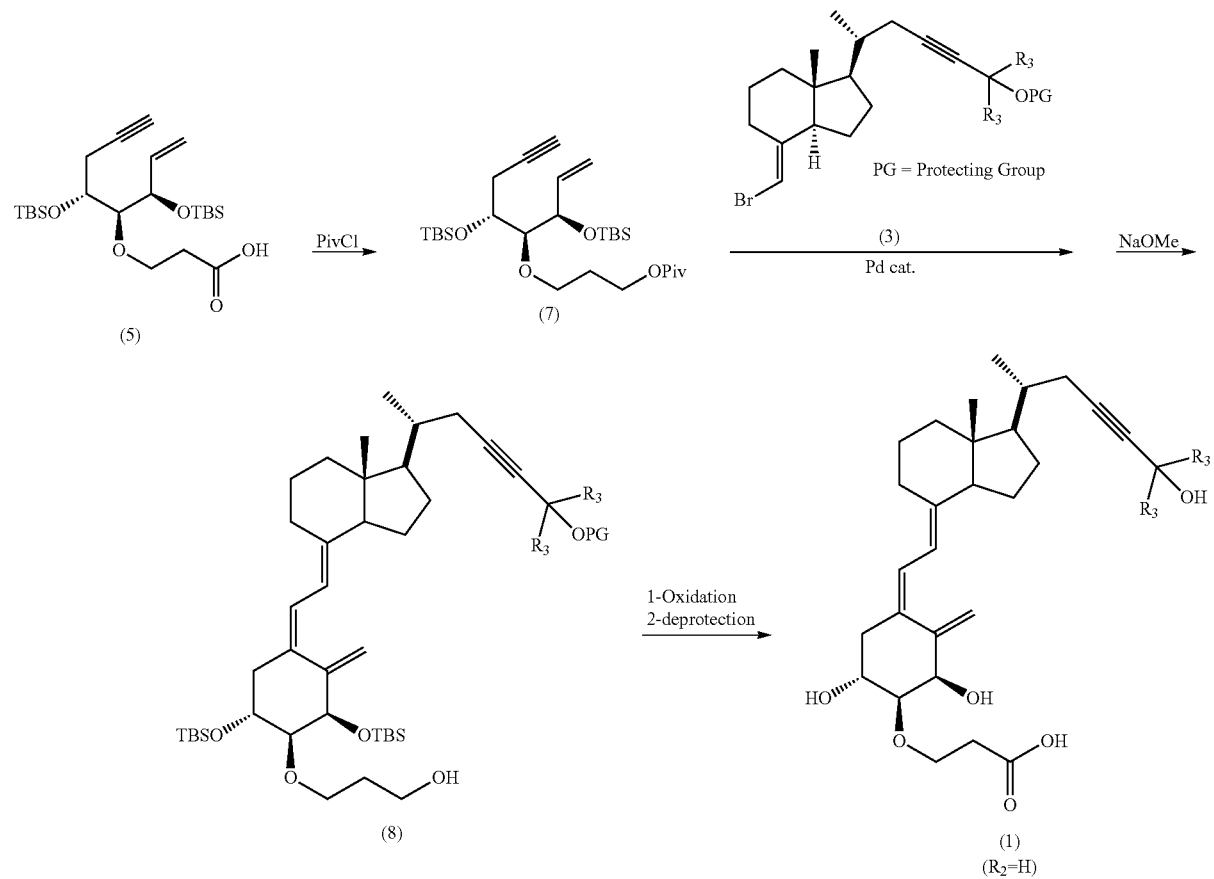

Further, in the above Scheme 1, when $R_2$ is substituted, for example, when $R_2$ in compound (2) is forming a cycloalkyl group together with the other $R_2$ and the carbon atom to which they are bound to, compound (10) is obtained by epoxidizing commercial 4,6-O-benzylidene-α-D-methyl-glucopyranoside (9), which is used as the starting material, and subsequently carrying out ring opening of the epoxide under basic conditions, in the same way as the ene-yne compound (4) described in the literature (Takayama, et al., "Vitamin D Analog in Cancer Prevention and Therapy," Recent Results in Cancer Research, Vol. 164, Springer, pp. 289-317, 2003 and the like). After obtaining compound (11) by protection of the hydroxyl groups of compound (10), ring opening of the benzylidene ring and, further, reduction of 1-position of glucose were carried out to obtain compound (12). Subsequently, an epoxide is formed from the diol portion to obtain compound (13), followed by reaction of the epoxide with acetylene to obtain compound (14) having a triple bond site introduced. By suitably protecting the hydroxyl groups, compound (15) can be obtained. By coupling of the compound (15) and the CD ring intermediate (3) described in Scheme 1 and selective deprotection, there is obtained compound (16). Further, by oxidation of the primary hydroxyl group to a carboxylic acid and subsequent deprotection of the protected hydroxyl groups, there can be obtained the desired compound (1).

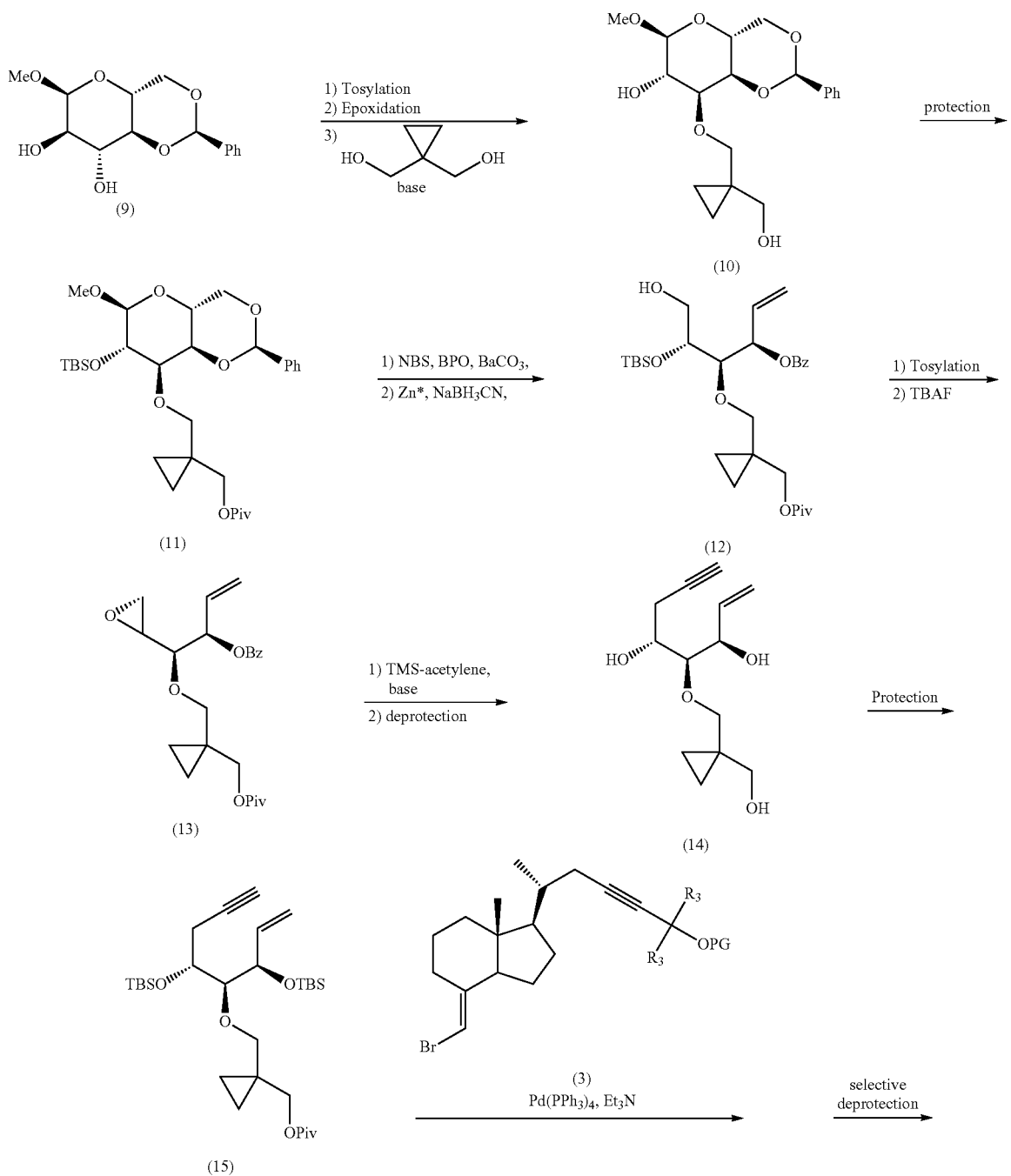

Scheme 5

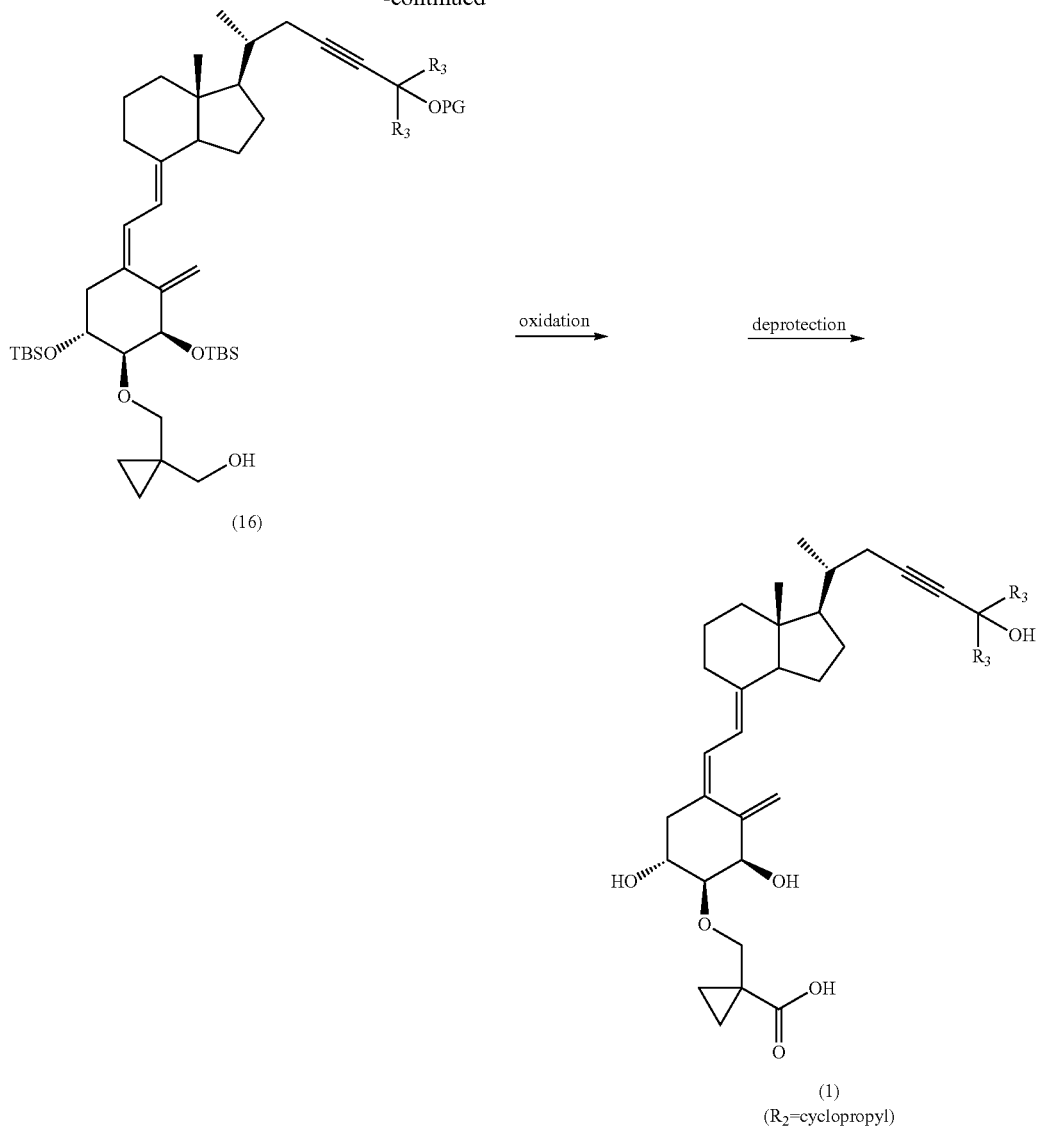

A therapeutic agent for osteoporosis and the like, comprising the vitamin $D_3$ derivative or a medicinally acceptable solvate thereof of the present invention as an active ingredient, is prepared by using a carrier, a vehicle, and other additives used commonly in drug formulation. The carrier and vehicle for drug formulation may be either solid or liquid, and include, for example, lactose, magnesium stearate, starch, talc, gelatin, agar, gum arabic, olive oil, sesame oil, cacao butter, ethylene glycol, and the like; and other commonly used materials. The mode of administration may be either oral administration by means of tablets, pills, capsules, granules, powder, fluids, and the like; or parenteral administration by means of injections such as intravenous injection, intramuscular injection, and the like, suppositories, transdermal drugs, and the like.

In the therapeutic agent of the present invention, a therapeutically effective amount of the active ingredient varies depending on the route of administration, age and gender of the patient, and extent of the disease.

However, it is generally about 0.01 to 10 μg/day and the number of doses is generally 1 to 3 times/day or 1 to 3 times/week. Thus, the formulation is preferably prepared to satisfy these conditions.

EXAMPLES

Hereinafter, the present invention will be described in more detail with reference to Examples. However, it should be understood that the present invention is not deemed to be limited thereto. In addition, abbreviations used in the present invention are as follows:
TBS=t-butyldimethylsilyl group;
TES=triethylsilyl group;
TESCl=chlorotriethylsilane;
TMS=trimethylsilyl group;
TMSCl=chlorotrimethylsilane;
Piv=pivaloyl group;
PivCl=pivaloyl chloride;
TBAF=tetrabutylammonium fluoride;
CSA=(+/−)-camphor-10-sulfonic acid;
PDC=pyridinium dichromate;
TBSOTf=t-butyldimethylsilyl trifluoromethanesulfonate;

DIBAL=dibutylaluminum hydride;
DMF=N,N-dimethylformamide;
THF=tetrahydrofuran;
TsCl=p-toluenesulfonyl chloride; and
Ts=p-toluenesulfonyl.

Example 1

Production of (5Z,7E)-(1R,2S,3R,20R)-2-(2-carboxyethoxy)-23-yne-9,10-seco-5,7,10(19)-cholestatriene-1,3,25-triol (Compound C-1)

pivaloyl chloride (0.69 mL, 5.65 mmol) at 0° C., the reaction mixture was stirred at room temperature. Anhydrous methanol (3 mL) was added thereto and the mixture was stirred at room temperature for further 30 minutes. Thereto was added toluene and the mixture was concentrated under reduced pressure. To the residue obtained was added ethyl acetate, the mixture was washed with saturated aqueous sodium chloride, and the organic layer was dried over anhydrous magnesium sulfate. The organic layer was concentrated under reduced pressure and the residue obtained was purified by silica gel

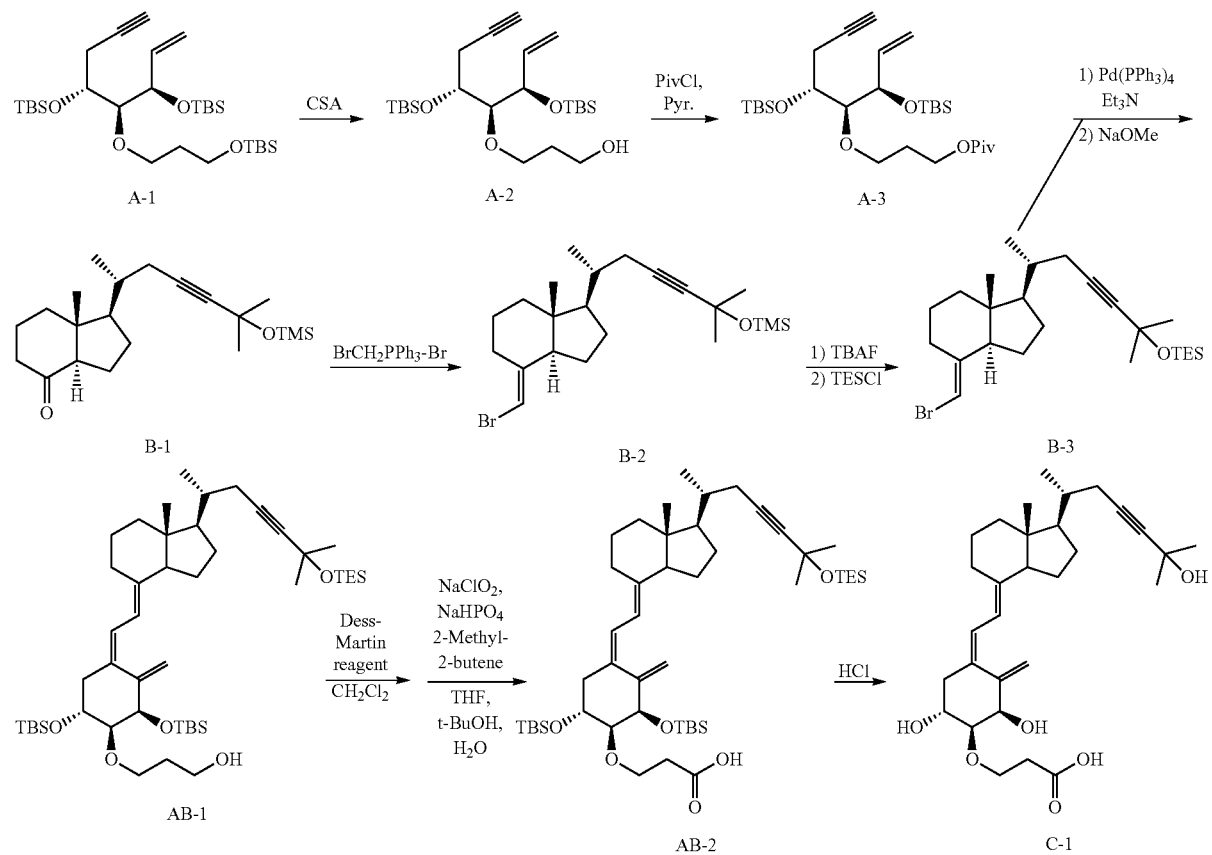

column chromatography (n-hexane/ethyl acetate=9/1) to obtain compound A-3 (1.072 g, yield 90%).

(1) Compound A-1 (2.29 g, 4.11 mmol), known in the literature (for example, Kittaka et al., J. Org. Chem., 69, 7463-7471 (2004)), was dissolved in ethanol (20 ml), thereto was added (+/−)-camphor-10-sulfonic acid (954 mg, 4.11 mmol) under ice cooling, and the mixture was stirred at 0° C. for 1 hour. The reaction was terminated by the addition of saturated aqueous sodium hydrogen carbonate and the mixture was diluted with ethyl acetate. This was washed with water and saturated aqueous sodium chloride and the organic layer was dried over anhydrous sodium sulfate. The organic layer was concentrated under reduced pressure and the residue obtained was purified by silica gel column chromatography (n-hexane/ethyl acetate=9/1) to obtain compound A-2 (1.64 g, yield 90%).

$^1$H-NMR (CDCl$_3$) δ: 5.96-5.88 (1H, m), 5.27-5.21 (2H, m), 4.29 (1H, dd, J=6.8, 3.9 Hz), 3.88-3.72 (5H, m), 3.45 (1H, dd, J=5.4, 4.1 Hz), 3.00 (1H, t, J=6.0 Hz), 2.50-2.46 (1H, m), 2.38-2.33 (1H, m), 2.01 (1H, t, J=2.6 Hz), 1.85-1.68 (2H, m), 0.91 (9H, s), 0.91 (9H, s), 0.10 (9H, s), 0.07 (3H, s).

(2) The compound A-2 (1.0 g, 2.26 mmol) obtained in (1) was dissolved in pyridine (10 ml) and, after the addition of $^1$H-NMR (CDCl$_3$) δ: 5.95 (1H, ddd, J=17.0, 11.0, 6.0 Hz), 5.21 (1H, ddd, J=17, 2.0, 1.0 Hz), 5.14 (1H, ddd, J=11.0, 2.0, 1.0 Hz), 4.32-4.28 (1H, m), 4.18-4.10 (2H, m), 3.86 (1H, q, J=5.6 Hz), 3.81-3.74 (1H, m), 3.68-3.60 (1H, m), 3.39 (1H, dd, J=5.4, 3.4 Hz), 2.49 (1H, dq, J=17.0, 2.7 Hz), 2.35 (1H, dq, J=16.9, 2.8 Hz), 1.96 (1H, t, J=2.7 Hz), 1.87 (2H, dt, J=14.0, 7.0 Hz), 1.19 (9H, s), 0.90 (9H, s), 0.89 (9H, s), 0.10 (3H, s), 0.08 (3H, s), 0.07 (5H, s), 0.03 (3H, s).

(3) (Bromomethyl)triphenylphophonium bromide (1.25 g, 2.87 mmol) was dissolved in tetrahydrofuran (7 ml) and the solution was cooled to 0° C. under a nitrogen atmosphere. Hereto was added sodium bis(trimethylsilyl)amide (1.0 M tetrahydrofuran solution, 2.90 mL, 2.87 mmol) and the mixture was stirred under ice cooling for 30 minutes. The reaction mixture was cooled to −78° C. and thereto was added a solution of compound B-1 (200 Mg, 0.574 mmol) dissolved in tetrahydrofuran, (1.5 mL) the compound being known in the literature (for example, Uskokovic et al., U.S. Pat. No.

4,804,502). After stirring at −78° C. for 1 hour, the mixture was stirred at 0° C. for further 1 hour. To the reaction mixture was added silica gel (2.5 g) and, after vigorous stirring at room temperature for 10 minutes, the mixture was filtered through celite. The filtrate obtained was concentrated under reduced pressure and the residue was purified by silica gel column chromatography (n-hexane/ethyl acetate=9/1) to obtain compound B-2 (161 mg, yield 67%).

$^1$H-NMR (CDCl$_3$) δ: 5.65 (1H, s), 2.90-2.86 (1H, m), 2.28-1.24 (20H, m), 1.08 (3H, d, J=6.3 Hz), 0.58 (3H, s), 0.18 (9H, s).

(4) The compound B-2 (1.2 g, 2.82 mmol) obtained in (3) was dissolved in tetrahydrofuran (10 mL), thereto was added tetrabutylammonium fluoride (1 M tetrahydrofuran solution, 4.23 mL, 4.23 mmol), and the mixture was stirred at 50° C. for 30 minutes. Thereto was added ethyl acetate, the mixture was washed with water, and the organic layer was dried over anhydrous magnesium sulfate. The organic layer was concentrated under reduced pressure and the residue obtained was purified by silica gel chromatography (n-hexane/ethyl acetate=19/1). The purified material was dissolved in anhydrous pyridine (10 mL) and the solution was cooled to 0° C. under a nitrogen atmosphere. Hereto was added chlorotriethylsilane (0.944 mL, 5.70 mmol) and the mixture was warmed to room temperature and stirred for 2.5 hours. The reaction mixture was cooled to 0° C. and, after the addition of saturated aqueous ammonium chloride and water, extraction was performed with toluene. The organic layer was washed with saturated aqueous sodium chloride and dried over anhydrous magnesium sulfate. The organic layer was concentrated under reduced pressure and the residue obtained was purified by silica gel chromatography (n-hexane/ethyl acetate=99/1) to obtain Compound B-3 (783 mg, yield 88%).

$^1$H-NMR (CDCl$_3$) δ: 5.65 (1H, s), 2.92-2.85 (1H, m), 2.23 (1H, dd, J=16.5, 3.4 Hz), 2.07-1.24 (19H, m), 1.08 (3H, d, J=6.6 Hz), 0.96 (9H, t, J=7.9 Hz), 0.66 (6H, q, J=7.9 Hz), 0.57 (3H, s).

(5) The compound B-3 (783 mg, 1.67 mmol) obtained in (4) and the compound A-3 (733 mg, 1.39 mmol) obtained in (2) were dissolved in anhydrous toluene/triethylamine (1/1, 11.1 mL), thereto was added tetrakis(triphenylphosphine)palladium (289 mg, 0.25 mmol), and the mixture was stirred under a nitrogen atmosphere at 105° C. for 2 hours. After cooling to room temperature, diamine silica gel (produced by Fuji Silysia Chemical Ltd., 6 g) and n-hexane (20 mL) were added thereto and the mixture was stirred at room temperature for 1 hour. Thereafter, the mixture was filtered by using ethyl acetate, the filtrate obtained was concentrated under reduced pressure, and the residue was purified by silica gel chromatography (n-hexane/ethyl acetate=100/0→95/5). The purified material obtained was dissolved in anhydrous tetrahydrofuran (5.5 mL) and anhydrous methanol (4.6 mL), thereto was added a methanol solution of sodium methoxide (0.91 mL, 5.46 mmol), and the mixture was refluxed for 1 hour. Saturated aqueous ammonium chloride was added and the mixture was concentrated under reduced pressure. To the residue obtained was added ethyl acetate, the mixture was washed with saturated aqueous sodium chloride, and the organic layer was dried over anhydrous magnesium sulfate. The organic layer was concentrated under reduced pressure and the residue obtained was purified by silica gel chromatography (n-hexane/ethyl acetate=100/0→50/50) to obtain compound AB-1 (609 mg, yield 67%).

$^1$H-NMR (CDCl$_3$) δ: 6.18 (1H, d, J=11.2 Hz), 6.02 (1H, d, J=11.2 Hz), 5.30 (1H, brs), 5.00 (1H, brs), 4.46 (1H, brs), 4.05 (1H, m), 3.88-3.69 (4H, m), 3.36 (1H, brs), 2.94 (1H, brs), 2.83-2.77 (1H, m), 2.62-2.56 (1H, m), 2.24 (1H, dd, J=16.5, 3.4 Hz), 2.10 (1H, dd, J=13.9, 4.4 Hz), 2.06-1.21 (21H, m), 1.07 (3H, d, J=6.6 Hz), 0.96 (9H, t, J=7.9 Hz), 0.93 (9H, s), 0.87 (9H, s), 0.67 (6H, q, J=7.9 Hz), 0.55 (3H, s), 0.10 (3H, s), 0.10 (3H, s), 0.08 (3H, s), 0.07 (3H, s).

(6) The compound AB-1 (427 mg, 0.514 mmol) obtained in (5) was dissolved in anhydrous dichloromethane (5.2 mL) and the solution was cooled to 0° C. Thereafter, Dess-Martin reagent (523 mg, 1.23 mmol) was added and, after stirring under ice cooling for 2 hours, the mixture was warmed to room temperature and stirred for 1 hour. Thereto were added saturated aqueous sodium thiosulfate and saturated aqueous sodium hydrogen carbonate, and the mixture was extracted with dichloromethane. The organic layer was washed with saturated aqueous sodium chloride, dried over anhydrous sodium sulfate, and concentrated under reduced pressure. The residue obtained was dissolved in t-butanol (21 mL), thereto were added tetrahydrofuran (37 mL) and 2-methyl-2-butene (6.47 mL), and the mixture was cooled with ice. An aqueous solution (7.3 mL) of sodium hypochlorite (purity 80%, 580 mg, 5.14 mmol) and sodium dihydrogen phosphate dihydrate (400 mg, 2.57 mmol) was added and the mixture was stirred under ice cooling for 45 minutes. Thereto were added saturated aqueous sodium thiosulfate and saturated aqueous sodium hydrogen carbonate, and the mixture was extracted with ethyl acetate. The organic layer was washed with saturated aqueous sodium chloride and dried over anhydrous sodium sulfate. The organic layer was concentrated under reduced pressure and the residue obtained was purified by silica gel chromatography (n-hexane/ethyl acetate=100/0→80/20) to obtain compound AB-2 (341 mg, yield 78%).

$^1$H-NMR (CDCl$_3$) δ: 6.22 (1H, d, J=11.2 Hz), 6.00 (1H, d, J=11.2 Hz), 5.27 (1H, brs), 4.99 (1H, brs), 4.45 (1H, brs), 4.07 (1H, m), 3.91 (2H, t, J=6.1 Hz), 3.36 (1H, brs), 2.84-2.77 (1H, m), 2.64 (2H, d, J=6.1, 1.5 Hz), 2.60-2.53 (1H, m), 2.24 (1H, dd, J=16.5, 3.4 Hz), 2.13 (1H, dd, J=13.9, 5.4 Hz), 2.07-1.21 (19H, m), 1.07 (3H, d, J=6.3 Hz), 0.96 (9H, t, J=7.9 Hz), 0.90 (9H, s), 0.87 (9H, s), 0.67 (6H, q, J=7.9 Hz), 0.55 (3H, s), 0.09 (3H, s), 0.09 (6H, s), 0.07 (3H, s).

(7) The compound AB-2 (140 mg, 0.165 mmol) obtained in (6) was dissolved in acetone (1.65 mL) and the solution was cooled to 0° C. Thereafter, a diluted solution (1.65 mL) of hydrochloric acid (6N, 0.332 mL) in acetone was added and the mixture was stirred at room temperature for 4 hours. Thereto was added n-hexane (3.3 mL) and the mixture was roughly purified by silica gel chromatography (n-hexane/acetone=1/1) and thin layer silica gel chromatography (n-hexane/acetone=4/5), and further purified by reversed-phase HPLC (A=0.1% formic acid/1% methanol/4% acetonitrile/water; B=0.1% formic acid/5% water/19% methanol/acetonitrile; 0-2 min.: B=20%, 2-20 min.: B=20%→98%, 20-25 min.: B=98%, 25-30 min.: B=20%) to obtain compound C-1 (34.9 mg, yield 42%).

$^1$H-NMR (CDCl$_3$) δ: 6.42 (1H, d, J=11.2 Hz), 6.00 (1H, d, J=11.2 Hz), 5.39 (1H, d, J=1.9 Hz), 5.09 (1H, d, J=1.9 Hz), 4.50 (1H, d, J=2.9 Hz), 4.36-3.58 (6H, m), 3.35 (1H, dd, J=8.1, 3.2 Hz), 2.86-2.79 (1H, m), 2.72-2.57 (3H, m), 2.29-2.19 (2H, m), 2.04-1.20 (19H, m), 1.06 (3H, d, J=6.6 Hz), 0.54 (3H, s).

Example 2

Production of (5Z,7E)-(1R,2S,3R,20R)-2-(2-methoxycarbonylethoxy)-23-yne-9,10-seco-5,7,10(19)-cholestatriene-1,3,25-triol (Compound C-2)

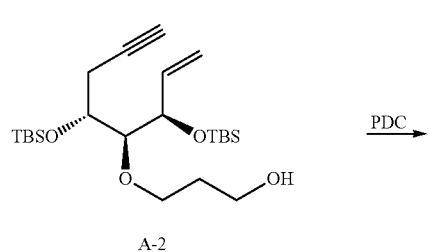

A-2

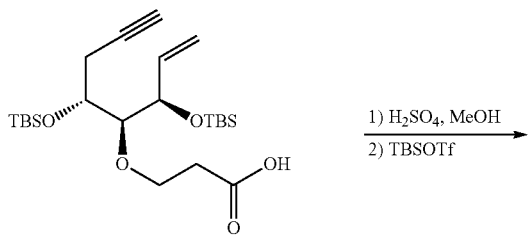

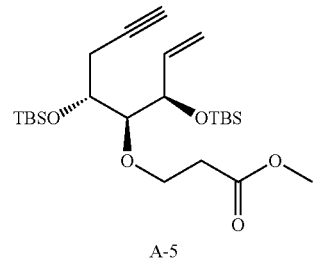

A-5

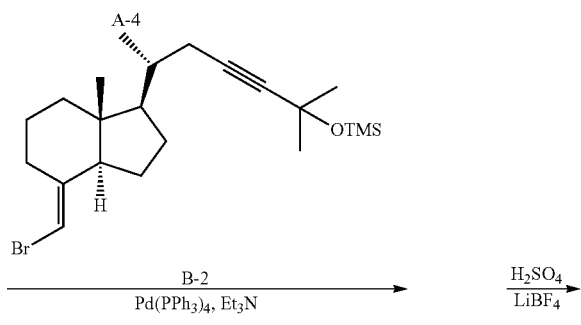

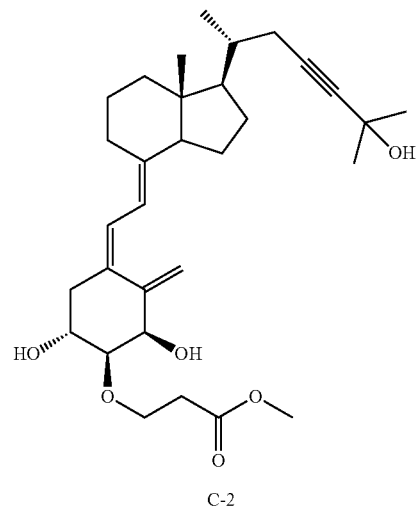

C-2

(1) The compound A-2 (1.45 g, 3.27 mmol) obtained in Example 1 (1) was dissolved anhydrous dimethylformamide (15 mL), thereto was added pyridinium dichromate (6.17 g, 16.4 mmol), and the mixture was stirred for 12 hours. Water was added, the mixture was extracted with ethyl acetate, and the organic layer obtained was dried over anhydrous magnesium sulfate. The organic layer was concentrated under reduced pressure and the residue obtained was purified by silica gel column chromatography (20% ethyl acetate/n-hexane) to obtain compound A-4 (0.82 g, yield 55%).

$^1$H-NMR (CDCl$_3$) δ: 5.90 (1H, ddd, J=17.0, 6.0, 11.0 Hz), 5.30-5.20 (2H, m), 4.33 (1H, ddt, J=7.0, 3.0, 1.0 Hz), 3.96 (2H, td, J=6.0, 1.2 Hz), 3.85-3.75 (1H, m), 3.55 (1H, dd, J=6.3, 3.7 Hz), 2.63 (2H, td, J=5.9, 1.9 Hz), 2.50-2.32 (2H, m), 2.02 (1H, t, J=2.7 Hz), 0.91 (9H, s), 0.90 (9H, s), 0.11 (3H, s), 0.10 (3H, s), 0.09 (3H, s), 0.08 (3H, s).

(2) The compound A-4 (0.82 g, 1.79 mmol) obtained in (1) was dissolved in anhydrous methanol (8 mL), thereto was added concentrated sulfuric acid (74 μL, 1.5 mmol), and the mixture was stirred for 2.5 hours. After cooling to room temperature, saturated aqueous sodium hydrogen carbonate was added thereto and the mixture was extracted with ethyl acetate. The organic layer obtained was dried over anhydrous sodium sulfate and concentrated under reduced pressure. The residue was dissolved in anhydrous dichloromethane, thereto were added under ice cooling 2,6-lutidine (1.01 mL, 9 mmol) and t-butyldimethylsilyl trifluoromethanesulfonate (1.65 mL, 7.2 mmol), and thereafter the mixture was stirred at room temperature for 1 hour. Anhydrous methanol (1.5 mL) was added and the mixture was stirred at room temperature for further 10 minutes. Thereto was added n-hexane/ethyl acetate (9/1), the mixture was washed with water, and the organic layer obtained was dried over anhydrous sodium sulfate. The organic layer was concentrated under reduced pressure and the residue was purified by silica gel column chromatography (3% ethyl acetate/n-hexane) to obtain compound A-5 (683.4 mg, yield 81%).

$^1$H-NMR (CDCl$_3$) δ: 5.94 (1H, ddd, J=10.0, 17.2, 6.5 Hz), 5.21 (1H, dt, J=17.3, 1.3 Hz), 5.14 (1H, dt, J=10.0, 1.3 Hz), 4.30 (1H, dd, J=6.8, 3.4 Hz), 4.00-3.97 (1H, m), 3.88-3.82 (2H, m), 3.68 (3H, s), 3.40 (1H, dd, J=5.5, 3.5 Hz), 2.57 (2H, t, J=6.6 Hz), 2.48 (1H, dq, J=16.8, 2.7 Hz), 2.35 (1H, dq, J=17.0, 2.8 Hz), 1.96 (1H, t, J=2.6 Hz), 0.90 (9H, s), 0.89 (9H, s), 0.09 (3H, s), 0.08 (3H, s), 0.07 (3H, s), 0.03 (3H, s).

(3) The compound A-5 (47.0 mg, 0.1 mmol) obtained in (2) and the compound B-2 (46.2 mg, 0.11 mmol) obtained in Example 1 (3) were dissolved in toluene/triethylamine (1/1, 2 mL), thereto was added tetrakis(triphenylphosphine)palladium (12.5 mg, 0.0108 mmol), and the mixture was stirred under a nitrogen atmosphere at 110° C. for 3 hours. The mixture was cooled to room temperature and concentrated under reduced pressure. The residue was roughly purified by thin layer silica gel chromatography (n-hexane/ethyl acetate=19/1). The crude purified material obtained was dissolved in anhydrous dichlotomethane/acetonitrile (1/1, 1 mL), thereto were added at 0° C. under a nitrogen atmosphere lithium tetrafluoroborate (78 mg, 0.8 mmol) and sulfuric acid (1 M acetonitrile solution, 0.08 mL, 0.08 mmol), and the mixture was stirred for 30 minutes. Thereto was added saturated aqueous sodium hydrogen carbonate and the mixture was extracted with ethyl acetate. The organic layer obtained was washed with saturated aqueous sodium chloride and dried over anhydrous sodium sulfate. The organic layer was concentrated under reduced pressure and the residue obtained was roughly purified by thin layer silica gel chromatography (n-hexane/ethyl acetate=1/2) and further purified by reversed-phase HPLC (A=95% water/acetonitrile; B=0.5% water/40% methanol/acetonitrile; B=75%) to obtain compound C-2 (6.8 mg, 13%).

$^1$H-NMR (CDCl$_3$) δ: 6.42 (1H, d, J=11.2 Hz), 6.03 (1H, d, J=11.2 Hz), 5.40 (1H, d, J=1.2 Hz), 5.09 (1H, d, J=2.2 Hz), 4.45 (1H, t, J=3.3 Hz), 4.06-3.79 (3H, m), 3.73 (3H, s), 3.36 (1H, dd, J=7.7, 3.3 Hz), 2.85-2.60 (7H, m), 2.24 (2H, dt, J=18.8, 5.9 Hz), 2.02-1.96 (3H, m), 1.89-1.82 (2H, m), 1.72-1.54 (6H, m), 1.51 (6H, s), 1.47-1.24 (4H, m), 1.06 (3H, d, J=6.3 Hz), 0.54 (3H, s).

MS m/z 537.2 (M+23)+ 523.3 (M+18)+

Example 3

Production of (5Z,7E)-(1R,2S,3R,20R)-2-(2-propoxycarbonylethoxy)-23-yne-9,10-seco-5,7,10(19)-cholestatriene-1,3,25-triol (Compound C-4)

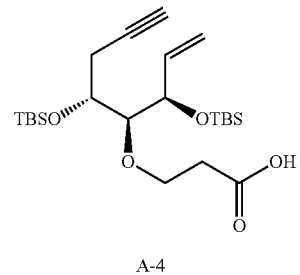

A-4

1) H$_2$SO$_4$, PrOH
2) TBSOTf

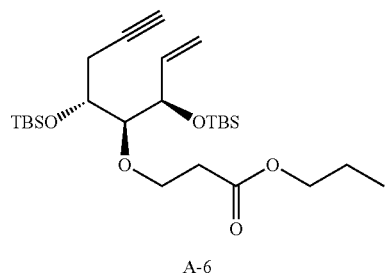

A-6

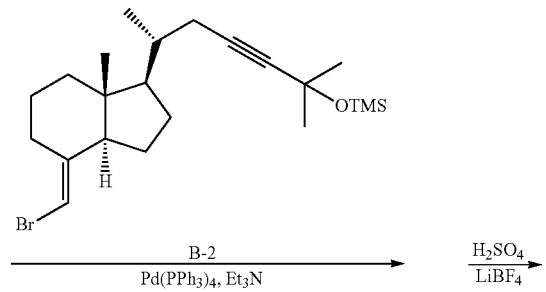

B-2
Pd(PPh$_3$)$_4$, Et$_3$N

H$_2$SO$_4$
LiBF$_4$

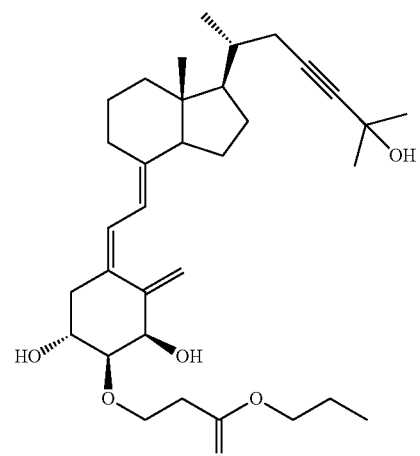

C-4

(1) Using the compound A-4 (240 mg, 0.525 mmol) obtained in Example 2 (1) as a raw material and replacing methanol with propanol, synthesis was carried out in the same manner as in Example 2 (2) to obtain compound A-6 (18.5 mg, yield 27%).

(2) Using the compound A-6 (40.5 mg, 0.081 mmol) obtained in (1) and the compound B-2 (47 mg, 0.11 mmol) obtained in Example 1 (3) as raw materials, synthesis was carried out in the same manner as in Example 2 (3) to obtain compound C-4 (6.8 mg, yield 15%).

1H-NMR (CDCl3) δ: 6.42 (1H, d, J=11.2 Hz), 6.03 (1H, d, J=11.2 Hz), 5.39 (1H, d, J=1.2 Hz), 5.09 (1H, d, J=2.2 Hz), 4.45 (1H, t, J=3.5 Hz), 4.08 (2H, t, J=6.7 Hz), 4.06-3.95 (2H, m), 3.85-3.77 (1H, m), 3.36 (1H, dd, J=7.8, 3.2 Hz), 2.85-2.82 (1H, m), 2.79 (1H, d, J=4.1 Hz), 2.70-2.62 (4H, m), 2.26-2.22 (2H, m), 2.03-1.98 (3H, m), 1.90-1.80 (3H, m), 1.70-1.64 (7H, m), 1.58-1.53 (4H, m), 1.51 (6H, s), 1.48-1.45 (2H, m), 1.40-1.20 (4H, m), 1.06 (3H, d, J=6.6 Hz), 0.94 (4H, t, J=7.4 Hz), 0.54 (3H, s).

Example 4

Production of (5Z,7E)-(1R,2S,3R,20R)-2-(2-(1-methyl)ethoxycarbonylethoxy)-23-yne-9,10-seco-5,7,10(19)-cholestatriene-1,3,25-triol (Compound C-5)

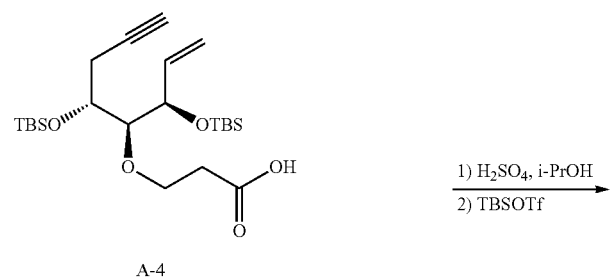

A-4

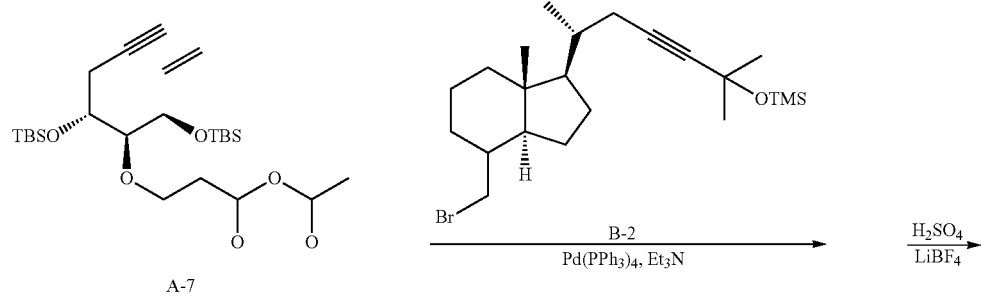

A-7

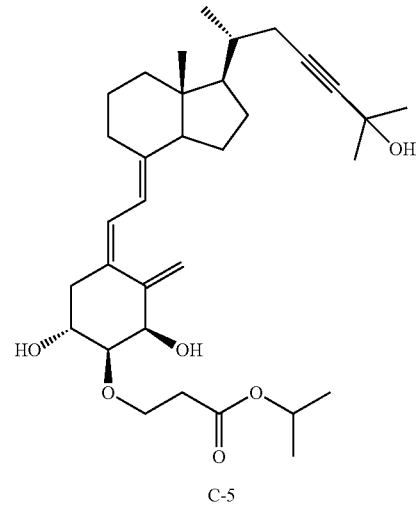

C-5

(1) Using the compound A-4 (240 mg, 0.525 mmol) obtained in Example 2 (1) as a raw material and replacing methanol with isopropanol, synthesis was carried out in the same manner as in Example 2 (2) to obtain compound A-7 (157.4 mg, yield 60%).

(2) Using the compound A-7 (35 mg, 0.07 mmol) obtained in (1) and the compound B-2 (44 mg, 0.11 mmol) obtained in Example 1 (3) as raw materials, synthesis was carried out in the same manner as in Example 2 (3) to obtain compound C-5 (6.8 mg, yield 17%).

1H-NMR (CDCl3) δ: 6.42 (1H, d, J=11.0 Hz), 6.03 (1H, d, J=11.5 Hz), 5.39 (1H, d, J=1.5 Hz), 5.09-5.02 (2H, m), 4.45 (1H, t, J=3.5 Hz), 4.05-3.78 (3H, m), 3.35 (1H, dd, J=7.7, 3.3 Hz), 2.85-2.58 (6H, m), 2.28-1.53 (18H, m), 1.51 (6H, s), 1.46-1.30 (5H, m), 1.26 (3H, d, J=1.7 Hz), 1.24 (3H, d, J=1.5 Hz), 1.06 (3H, d, J=6.3 Hz), 0.54 (3H, s).

Example 5

Production of (5Z,7E)-(1S,2S,3R,20R)-2-(2-carboxypropyl)-23-yne-9,10-seco-5,7,10(19)-cholestatriene-1,3,25-triol (Compound D-1)

Thereto were added at 0° C. triethylamine (0.47 mL, 3.37 mmol), trimethylamine hydrochloride (16 mg, 0.169 mmol), and p-toluenesulfonyl chloride (0.48 g, 2.53 mmol) and the mixture was stirred at room temperature for 1 hour. Saturated aqueous sodium hydrogen carbonate was added thereto, the mixture was extracted with ethyl acetate, and the organic layer was dried over anhydrous magnesium sulfate. The organic layer was concentrated under reduced pressure and the residue obtained was dissolved in dimethylformamide (3 mL). Thereto were added sodium cyanide (199 mg, 4.06 mmol) and sodium iodide (380 mg, 2.53 mmol), and the mixture was stirred at 50° C. for 2 hours. Water was added and the mixture was extracted with ethyl acetate. The organic layer was washed with saturated aqueous sodium chloride, dried over anhydrous magnesium sulfate, and concentrated under reduced pressure to obtain crude compound A-9. This was dissolved in tetrahydrofuran (5 mL), thereto was added tetrabutylammonium fluoride (1 M tetrahydrofuran solution, 5.07 mL, 5.07 mmol), and the mixture was stirred at 60° C. for 1 hour. Ethyl acetate was added, the mixture was washed with water, and the organic layer was dried over anhydrous mag-

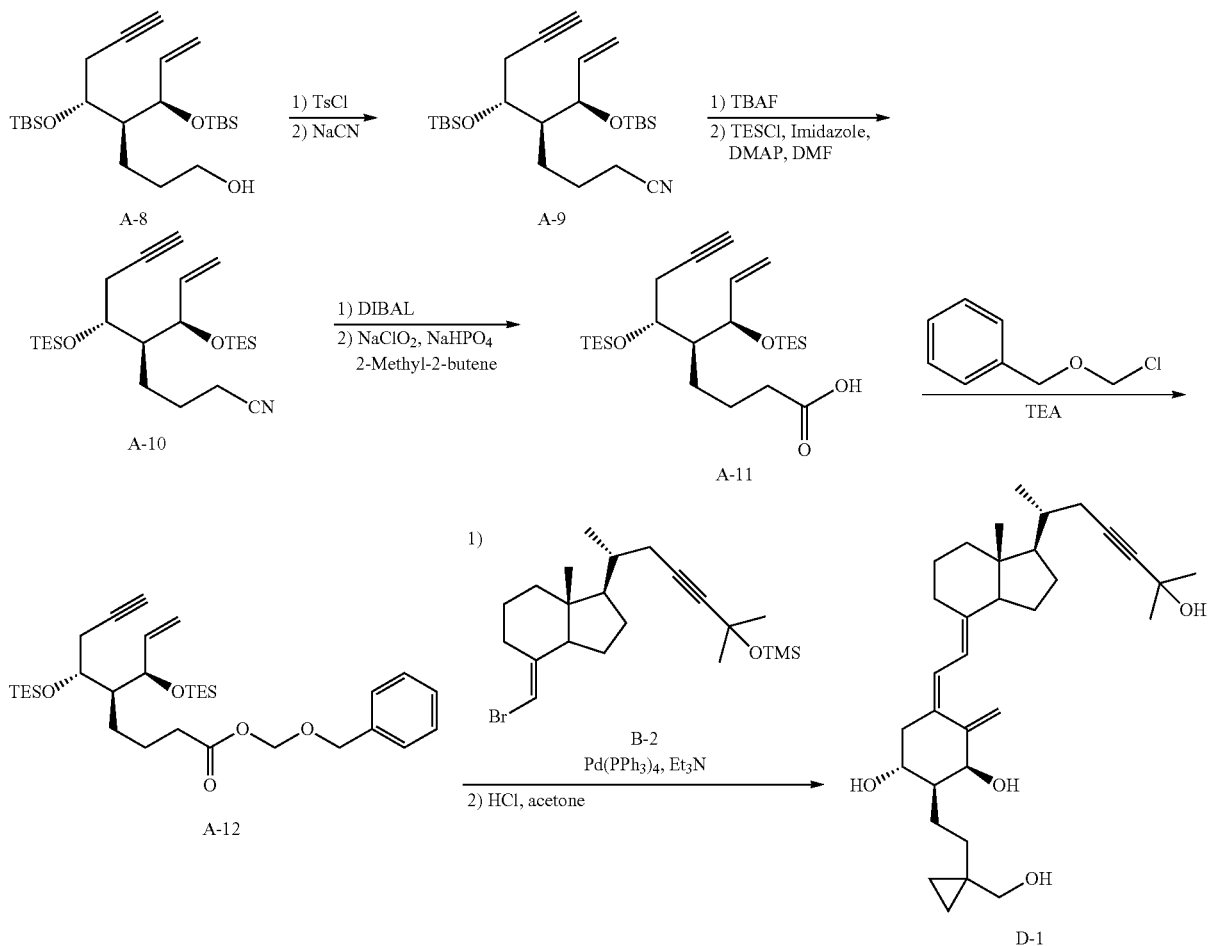

(1) Compound A-8 (0.72 g, 1.69 mmol), obtained from (3R,4R,5S)-3,5-bis[(t-butyldimethylsilyl)oxy]-4-[3-{(t-butyldimethylsilyl)oxy}propyl]oct-1-ene-7-yne, a compound known in the literature (for example, Saito, et al., Tetrahedron, 60, 7951-7961 (2004)) in the same manner as in Example 1 (1), was dissolved in dichloromethane (6.8 ml).

nesium sulfate and concentrated under reduced pressure. The residue obtained was dissolved in dimethylformamide (5 mL), thereto were added at 0° C. imidazole (460 mg, 6.76 mmol), dimethylaminopyridine (21 mg, 0.169 mmol), and chlorotriethylsilane (0.851 mL, 5.07 mmol), and the mixture was stirred at 50° C. for 40 minutes. Saturated aqueous sodium hydrogen carbonate was added thereto, the mixture was extracted with ethyl acetate, and the organic layer was dried over anhydrous magnesium sulfate. The organic layer was concentrated under reduced pressure and the residue obtained was purified by silica gel column chromatography (1% ethyl acetate/n-hexane→2% ethyl acetate/n-hexane→5% ethyl acetate/n-hexane→10% ethyl acetate/n-hexane) to obtain compound A-10 (531.3 mg, yield 72%).

$^1$H-NMR (CDCl$_3$) δ: 5.82 (1H, ddd, J=17.0, 10.0, 7.0 Hz), 5.17 (1H, dd, J=17.2, 1.1 Hz), 5.11 (1H, ddd, J=10.0, 2.0, 1.0 Hz), 4.00-3.95 (1H, m), 2.42-2.37 (2H, m), 2.32 (2H, t, J=7.8 Hz), 1.97 (1H, t, J=2.6 Hz), 1.85-1.65 (3H, m), 1.43-1.29 (2H, m), 1.26 (2H, t, J=7.2 Hz), 0.89 (19H, s), 0.09 (3H, s), 0.06 (3H, s), 0.06 (3H, s), 0.03 (3H, s).

(2) The compound A-10 (449.4 mg, 1.03 mmol) obtained in (1) was dissolved in dichloromethane (5 mL), thereto was added diisobutylaluminum hydride (1 M toluene solution, 2.08 mL, 2.08 mmol) under cooling at −78° C., and the mixture was stirred at −78° C. for 50 minutes. Anhydrous methanol (0.3 mL) was added and the mixture was stirred at room temperature for 20 minutes. Further, saturated aqueous sodium potassium tartrate was added and the mixture was stirred for 10 minutes. Ethyl acetate was added thereto, the mixture was washed with saturated aqueous sodium chloride, and the organic layer was dried over anhydrous magnesium sulfate and concentrated under reduced pressure. The residue obtained was dissolved in tetrahydrofuran (6.9 mL), thereto were added t-butanol (6.9 mL) and 2-methyl-2-butene (4.5 g), and the mixture was cooled with ice. An aqueous solution (6.9 mL) of sodium hypochlorite (931 mg, 10.3 mmol) and sodium dihydrogen phosphate (803 mg, 5.15 mmol) was added thereto and the mixture was stirred for 1 hour. This was followed by the addition of saturated aqueous sodium thiosulfate and, further, by the addition of saturated aqueous sodium hydrogen carbonate, and the mixture was extracted with ethyl acetate. The organic layer was washed with saturated aqueous sodium chloride, dried over anhydrous sodium sulfate, and concentrated under reduced pressure. The residue obtained was purified by silica gel chromatography (n-hexane/ethyl acetate=100/1→50/1→20/1→10/1→5/1→2/1) to obtain compound A-11 (220 mg, yield 47%).

$^1$H-NMR (CDCl$_3$) δ: 5.82 (1H, ddd, J=17.0, 10.0, 7.0 Hz), 5.17 (1H, dd, J=17.2, 1.1 Hz), 5.11 (1H, ddd, J=10.0, 2.0, 1.0 Hz), 4.00-3.95 (1H, m), 2.42-2.37 (2H, m), 2.32 (2H, t, J=7.8 Hz), 1.97 (1H, t, J=2.6 Hz), 1.85-1.65 (3H, m), 1.43-1.29 (2H, m), 1.26 (2H, t, J=7.2 Hz), 0.89 (19H, s), 0.09 (3H, s), 0.06 (3H, s), 0.06 (3H, s), 0.03 (3H, s).

(3) The compound A-11 (126.6 mg, 0.278 mmol) obtained in (2) was dissolved in dimethylformamide (1.2 mL), thereto was added triethylamine (0.126 mL, 0.9 mmol) under cooling at 0° C., and the mixture was stirred for 40 minutes. Thereto was added saturated aqueous sodium hydrogen carbonate and the mixture was extracted with ethyl acetate. The organic layer was dried over anhydrous magnesium sulfate and concentrated under reduced pressure. The residue obtained was purified by silica gel chromatography (n-hexane/ethyl acetate=95/5) to obtain compound A-12 (126.5 mg, yield 79%).

$^1$H-NMR (CDCl$_3$) δ: 5.82 (1H, ddd, J=17.0, 10.0, 7.0 Hz), 5.17 (1H, dd, J=17.2, 1.1 Hz), 5.11 (1H, ddd, J=10.0, 2.0, 1.0 Hz), 4.00-3.95 (1H, m), 2.42-2.37 (2H, m), 2.32 (2H, t, J=7.8 Hz), 1.97 (1H, t, J=2.6 Hz), 1.85-1.65 (3H, m), 1.43-1.29 (2H, m), 1.26 (2H, t, J=7.2 Hz), 0.89 (19H, s), 0.09 (3H, s), 0.06 (3H, s), 0.06 (3H, s), 0.03 (3H, s).

(4) The compound A-12 (46 mg, 0.08 mmol) obtained in (3) above and the compound B-2 (47 mg, 0.1 mmol) obtained in Example 1 (3) were dissolved in toluene/triethylamine (1/1, 0.2 mL), thereto was added tetrakis(triphenylphosphine)palladium (12 mg, 0.01 mmol), and the mixture was stirred under a nitrogen atmosphere at 110° C. for 3 hours. The mixture was cooled to room temperature and, thereafter, concentrated under reduced pressure. The residue was roughly purified by thin-layer silica gel column chromatography (n-hexane/ethyl acetate=19/1). The crude purified material obtained was dissolved in acetone, hydrochloric acid (6 N, 0.1 mL, 0.6 mmol) was added thereto, and the mixture was stirred at 0° C. for 50 minutes. Further, hydrochloric acid (6 N, 0.2 mL, 1.2 mmol) was added, and the mixture was stirred at room temperature for 40 minutes. Thereto was added saturated aqueous sodium hydrogen carbonate and the mixture was extracted with ethyl acetate. The organic layer was dried over anhydrous magnesium sulfate, concentrated under reduced pressure, and the residue obtained was roughly purified by Bond Elut SI (produced by Varian, Inc.; n-hexane/ethyl acetate=1/2→ethyl acetate→ethyl acetate/acetic acid=99/1). The crude purified material was further purified by reversed-phase HPLC (A=95% water/acetonitrile; B=0.5% acetic acid/5% water/acetonitrile; B=65%) to obtain compound D-1 (14.6 mg, 36%).

$^1$H-NMR (CDCl$_3$) δ: 6.40 (1H, d, J=11.5 Hz), 6.00 (1H, d, J=11.2 Hz), 5.27 (1H, d, J=1.5 Hz), 4.99 (1H, d, J=2.0 Hz), 4.39 (1H, t, J=4.0 Hz), 3.92-3.84 (1H, m), 2.86-2.79 (1H, m), 2.65 (1H, dd, J=13.3, 4.3 Hz), 2.30-2.20 (4H, m), 2.05-1.96 (3H, m), 1.88 (2H, t, J=10.0 Hz), 1.81-1.64 (8H, m), 1.56 (6H, dt, J=15.3, 4.5 Hz), 1.51 (6H, s), 1.49-1.46 (3H, m), 1.45 (9H, s), 1.40-1.24 (5H, m), 1.06 (3H, d, J=6.6 Hz), 0.54 (3H, s), 0.54 (3H, s).

Example 6

Production of (5Z,7E)-(1S,2S,3R,20R)-2-(2-(1,1-dimethyl)ethoxycarbonylpropyl)-23-yne-9,10-seco-5,7,10(19)-cholestatriene-1,3,25-triol (Compound D-6)

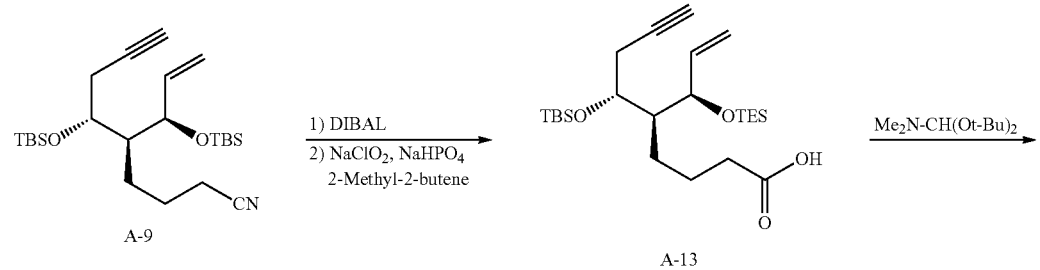

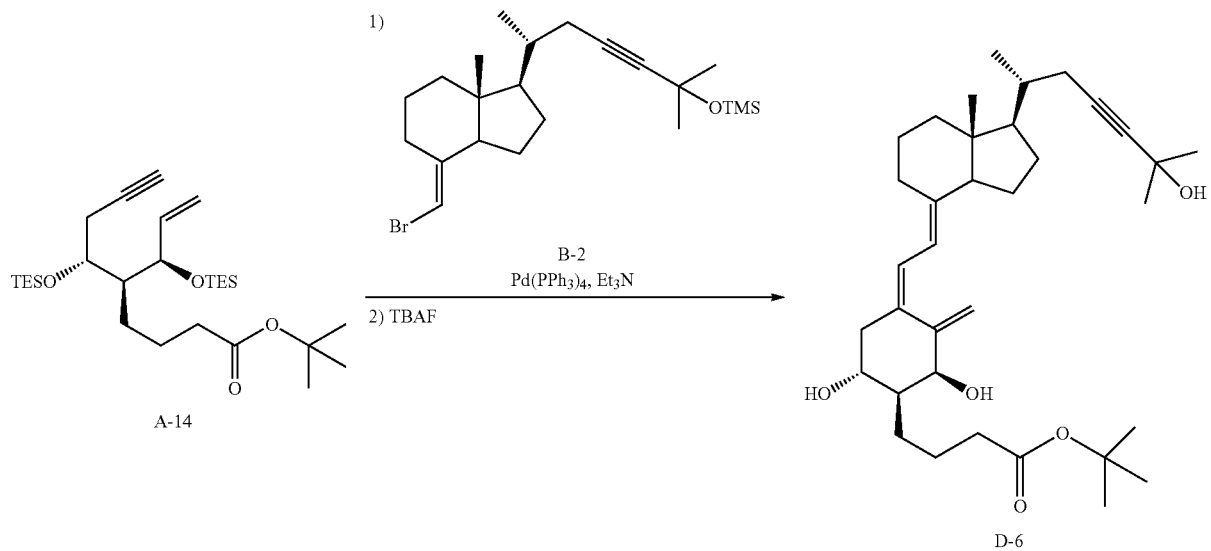

(1) The compound A-9 (565 mg, 1.29 mmol) obtained in Example 5 (1) was dissolved in dichloromethane, thereto was added diisobutylaluminum hydride (1 M toluene solution, 2 mL, 2 mmol) under cooling at −78° C., and the mixture was stirred at −78° C. for 2 hours. Anhydrous methanol (1 mL) was added and the mixture was stirred at room temperature for 20 minutes. Further, saturated aqueous sodium potassium tartrate was added and the mixture was stirred for 10 minutes. Ethyl acetate was added thereto, the mixture was washed with saturated aqueous sodium chloride, and the organic layer was dried over anhydrous magnesium sulfate and concentrated under reduced pressure. The residue obtained was dissolved in tetrahydrofuran (18.3 mL), thereto were added t-butanol (18.3 mL) and 2-methyl-2-butene (6 mL), and the mixture was cooled with ice. An aqueous solution (5 mL) of sodium hypochlorite (1.47 g, 13 mmol) and sodium dihydrogenphosphate (1.01 g, 6.5 mmol) was added thereto and the mixture was stirred for 1 hour. To the mixture were added saturated aqueous sodium thiosulfate and, further, saturated aqueous sodium hydrogen carbonate, and the mixture was extracted with ethyl acetate. The organic layer was washed with saturated aqueous sodium chloride, dried over anhydrous sodium sulfate, and concentrated under reduced pressure. The residue obtained was purified by silica gel chromatography (n-hexane/ethyl acetate=9/1→7/1→5/1) to obtain compound A-13 (233.7 mg, yield 38%).

$^1$H-NMR (CDCl$_3$) δ: 5.82 (1H, ddd, J=17.0, 10.0, 7.0 Hz), 5.17 (1H, dd, J=17.2, 1.1 Hz), 5.11 (1H, ddd, J=10.0, 2.0, 1.0 Hz), 4.00-3.95 (1H, m), 2.42-2.37 (2H, m), 2.32 (2H, t, J=7.8 Hz), 1.97 (1H, t, J=2.6 Hz), 1.85-1.65 (3H, m), 1.43-1.29 (2H, m), 1.26 (2H, t, J=7.2 Hz), 0.89 (19H, s), 0.09 (3H, s), 0.06 (3H, s), 0.06 (3H, s), 0.03 (3H, s).

(2) To the compound A-13 (228.4 mg, 0.5 mmol) obtained in (1) were added toluene (5 mL) and N,N-dimethylformamide di-t-butyl acetal (1.1 mL, 4 mmol), and the mixture was stirred at 80° C. for 1 hour. Thereto was added ethyl acetate, the mixture was washed with saturated aqueous sodium chloride, and the organic layer was dried over anhydrous magnesium sulfate. The organic layer was concentrated under reduced pressure and the residue obtained was purified by silica gel chromatography (3% ethyl acetate/n-hexane) to obtain compound A-14 (118.5 mg, yield 46%).

$^1$H-NMR (CDCl$_3$) δ: 5.83 (1H, ddd, J=17.0, 10.0, 7.0 Hz), 5.15 (1H, dq, J=17.2, 1.0 Hz), 5.10 (1H, dq, J=10.0, 1.0 Hz), 4.12 (1H, dd, J=8.0, 5.0 Hz), 4.00 (1H, td, J=6.2, 3.8 Hz), 2.39 (2H, dd, J=6.1, 2.7 Hz), 2.17 (2H, t, J=8.0 Hz), 1.79-1.63 (3H, m), 1.44 (9H, s), 1.40-1.20 (4H, m), 0.89 (18H, s), 0.09 (3H, s), 0.06 (3H, s), 0.05 (3H, s), 0.03 (3H, s).

(3) The compound A-14 (59.6 mg, 0.12 mmol) obtained in (2) and the compound B-2 (60 mg, 0.14 mmol) obtained in Example 1 (3) were dissolved in toluene/triethylamine (1/1, 2 mL), thereto was added tetrakis(triphenylphosphine)palladium (17 mg, 0.0147 mmol), and the mixture was stirred under a nitrogen atmosphere at 110° C. for 3.5 hours. The mixture was cooled to room temperature and concentrated under reduced pressure. The residue was roughly purified by thin-layer silica gel chromatography (n-hexane/ethyl acetate=19/1). The crude purified material obtained was dissolved in tetrahydrofuran, tetrabutylammonium fluoride (1 M tetrahydrofuran solution, 0.84 mL, 0.84 mmol) was added thereto, and the mixture was stirred at 60° C. for 2 hours. Ethyl acetate was added, the mixture was washed with water, and the organic layer was dried over anhydrous magnesium sulfate. The organic layer was concentrated under reduced pressure and the residue obtained was roughly purified by thin-layer silica gel chromatography (n-hexane/ethyl acetate=1/1) and further purified by reversed-phase HPLC (A=95% water/acetonitrile; B=0.5% water/40% methanol/acetonitrile; B=85%) to obtain compound D-6 (5.0 mg, yield 7%).

$^1$H-NMR (CDCl$_3$) δ: 6.40 (1H, d, J=11.5 Hz), 6.00 (1H, d, J=11.2 Hz), 5.27 (1H, d, J=1.5 Hz), 4.99 (1H, d, J=2.0 Hz), 4.39 (1H, t, J=4.0 Hz), 3.92-3.84 (1H, m), 2.86-2.79 (1H, m), 2.65 (1H, dd, J=13.3, 4.3 Hz), 2.30-2.20 (4H, m), 2.05-1.96 (3H, m), 1.88 (2H, t, J=10.0 Hz), 1.81-1.64 (8H, m), 1.56 (6H, dt, J=15.3, 4.5 Hz), 1.51 (6H, s), 1.49-1.46 (3H, m), 1.45 (9H, s), 1.40-1.24 (5H, m), 1.06 (3H, d, J=6.6 Hz), 0.54 (3H, s), 0.54 (3H, s).

Example 7

Production of (5Z,7E)-(1R,2S,3R,20R)-2-((t-butyl-carbonyloxy)methoxycarbonylethoxy)-23-yne-9,10-seco-5,7,10(19)-cholestatriene-1,3,25-triol (Compound C-7)

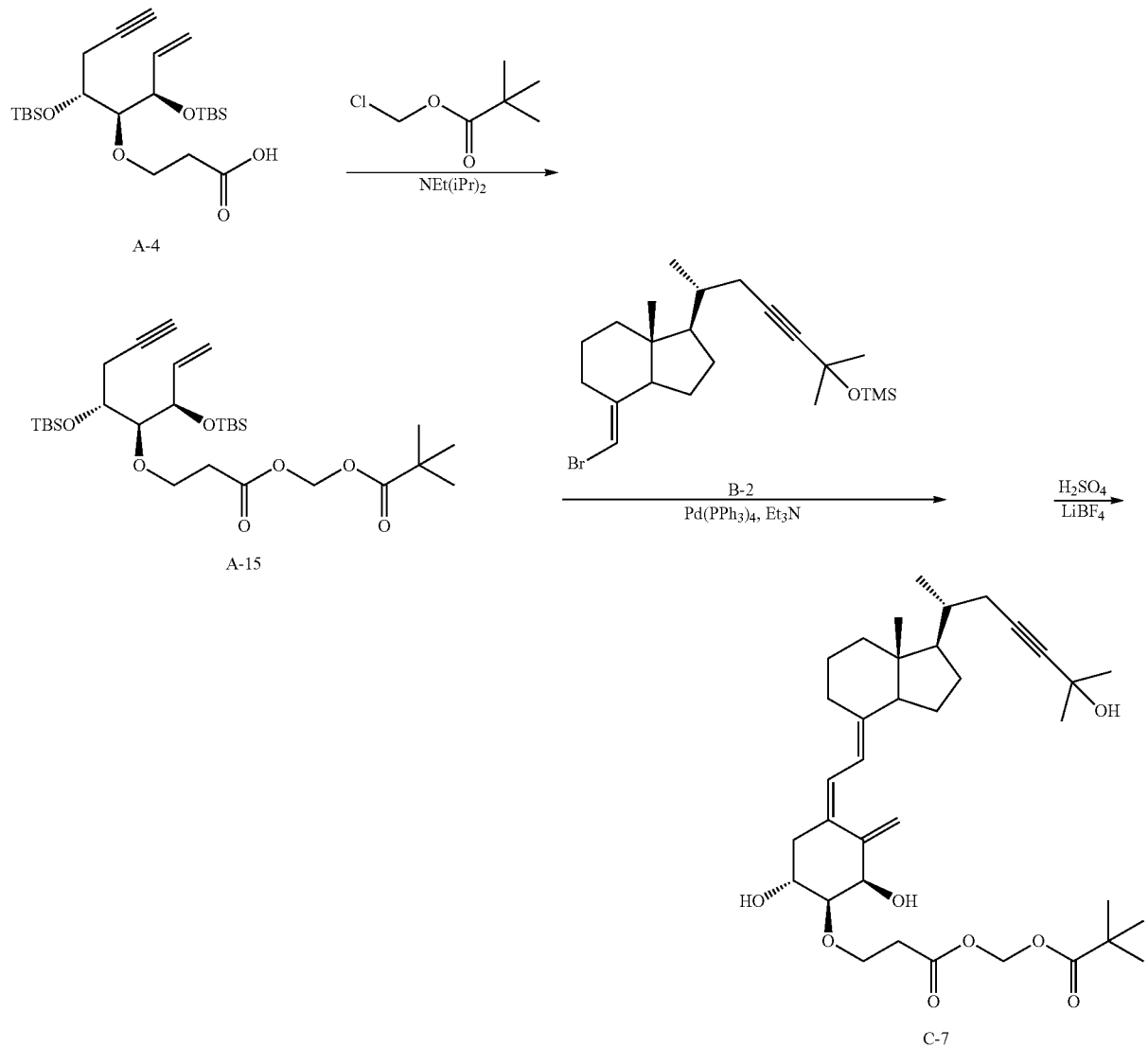

(1) The Compound A-4 (164.3 mg, 0.360 mmol) obtained in Example 2 (1) was dissolved in anhydrous N,N-dimethylformamide (1.2 mL) and the solution was cooled to 0° C. Triethylamine (0.15 mL, 1.08 mmol) and pivaloyloxymethyl chloride (0.104 mL, 0.719 mmol) were added thereto and the mixture was stirred at room temperature for 1 hour. After 1 hour, sodium iodide (150 mg, 1.008 mmol) and potassium carbonate (140 mg, 1.008 mmol) were added, and the mixture was stirred under heating at 50° C. for further 30 minutes. The reaction mixture was cooled to room temperature and, after dilution with water, the resulting mixture extracted with ethyl acetate. The organic layer was washed with saturated aqueous sodium chloride, dried over anhydrous magnesium sulfate, and thereafter concentrated under reduced pressure. The residue obtained was purified by silica gel column chromatography (n-hexane/ethyl acetate=5/1) to obtain compound A-15 (158.0 mg, yield 77%).

$^1$H-NMR (CDCl$_3$) δ: 5.98-5.90 (1H, m), 5.76 (2H, s), 5.21 (1H, dt, J=17.32, 1.46 Hz), 5.14 (1H, dt, J=10.37, 1.10 Hz), 4.30 (1H, dd, J=8.00, 3.00 Hz), 4.02-3.82 (3H, m), 3.42 (1H, dd, J=5.61, 3.41 Hz), 2.62 (2H, t, J=6.71 Hz), 2.47 (1H, ddd, J=16.83, 2.68, 5.50 Hz), 2.34 (1H, ddd, J=16.83, 2.76, 5.50 Hz), 1.96 (1H, t, J=2.68 Hz), 1.21 (9H, s), 0.90 (9H, s), 0.89 (9H, s), 0.09 (3H, s), 0.08 (3H, s), 0.07 (3H, s), 0.03 (3H, s).

(2) Using the compound A-15 (40 mg, 0.07 mmol) obtained in (1) and the compound B-2 (36 mg, 0.085 mmol) obtained in Example 1 (3) as raw materials, synthesis was carried out in the same manner as in Example 2 (3) to obtain compound C-7 (7.8 mg, yield 18%).

$^1$H-NMR (CDCl3) δ: 6.42 (1H, d, J=11.47 Hz), 6.02 (1H, d, J=11.22 Hz), 5.81-5.76 (2H, m), 5.39 (1H, d, J=1.46 Hz), 5.09 (1H, d, J=2.20 Hz), 4.44 (1H, s), 4.04-3.95 (2H, m), 3.85-3.80 (1H, m), 3.36 (1H, dd, J=7.56, 3.17 Hz), 2.85-2.57 (6H, m), 2.28-1.81 (8H, m), 1.59-1.24 (16H, m), 1.23 (9H, s), 1.06 (3H, d, J=6.59 Hz), 0.54 (3H, s).

Example 8

Production of (5Z,7E)-(1R,2S,3R,20R)-2-((phenylcarbonyloxy)methoxycarbonylethoxy)-23-yne-9,10-seco-5,7,10(19)-cholestatriene-1,3,25-triol (Compound C-8)

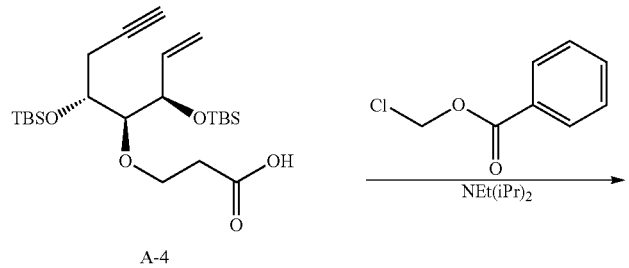

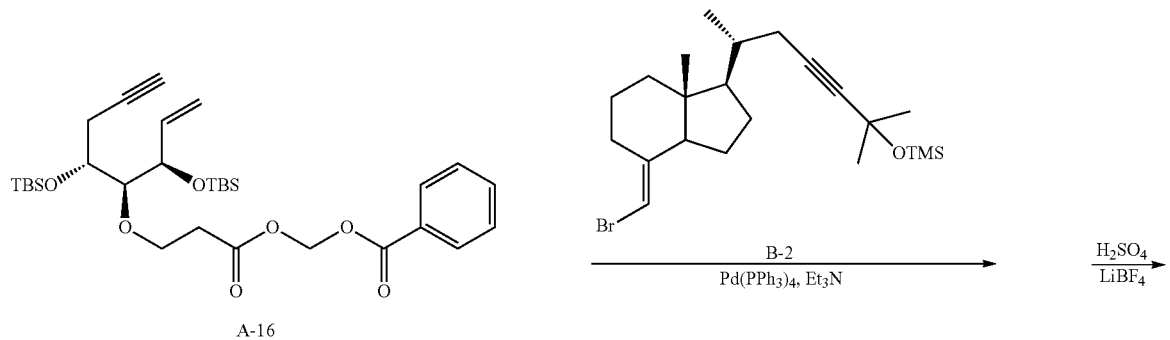

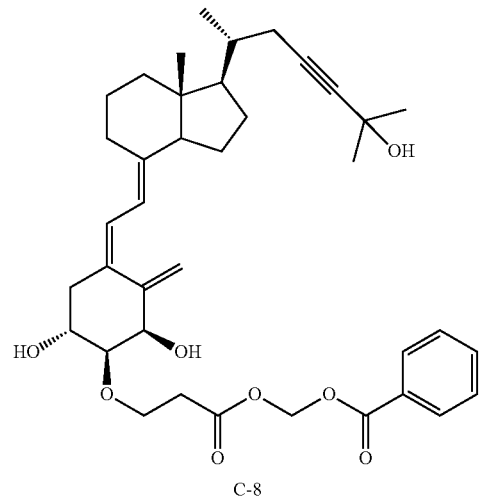

Using the compound A-4 (175 mg, 0.383 mmol) obtained in Example 2 (1) as a raw material and replacing pivaloyloxymethyl chloride with benzoyloxymethyl chloride, synthesis was carried out in the same manner as in Example 7 (1) to obtain compound A-16. Thereafter, using the compound A-16 (41.3 mg, 0.07 mmol) and the compound B-2 (34 mg, 0.08 mmol) obtained in Example 1 (3) as starting materials, synthesis was carried out in the same manner as in Example 7 (2) to obtain compound C-8 (4.9 mg, yield 11%).

1H-NMR (CDCl3) δ: 8.09-8.07 (2H, m), 7.62-7.44 (3H, m), 6.41 (1H, d, J=10.98 Hz), 6.05-6.01 (3H, m), 5.38 (1H, d, J=1.46 Hz), 5.07 (1H, d, J=1.95 Hz), 4.44 (1H, d, J=2.93 Hz), 4.05-3.97 (2H, m), 3.87-3.82 (1H, m), 3.36 (1H, dd, J=7.56, 3.17 Hz), 2.85-2.64 (4H, m), 2.32-2.18 (2H, m), 2.05-1.53 (9H, m), 1.49-1.24 (4H, m), 1.06 (3H, d, J=6.34 Hz), 0.55 (3H, s).

Example 9
Production of (5Z,7E)-(1R,2S,3R,20R)-2-((2-carboxy-2,2-ethano)ethoxy)-23-yne-9,10-seco-5,7,10(19)-cholestatriene-1,3,25-triol (Compound E-1)
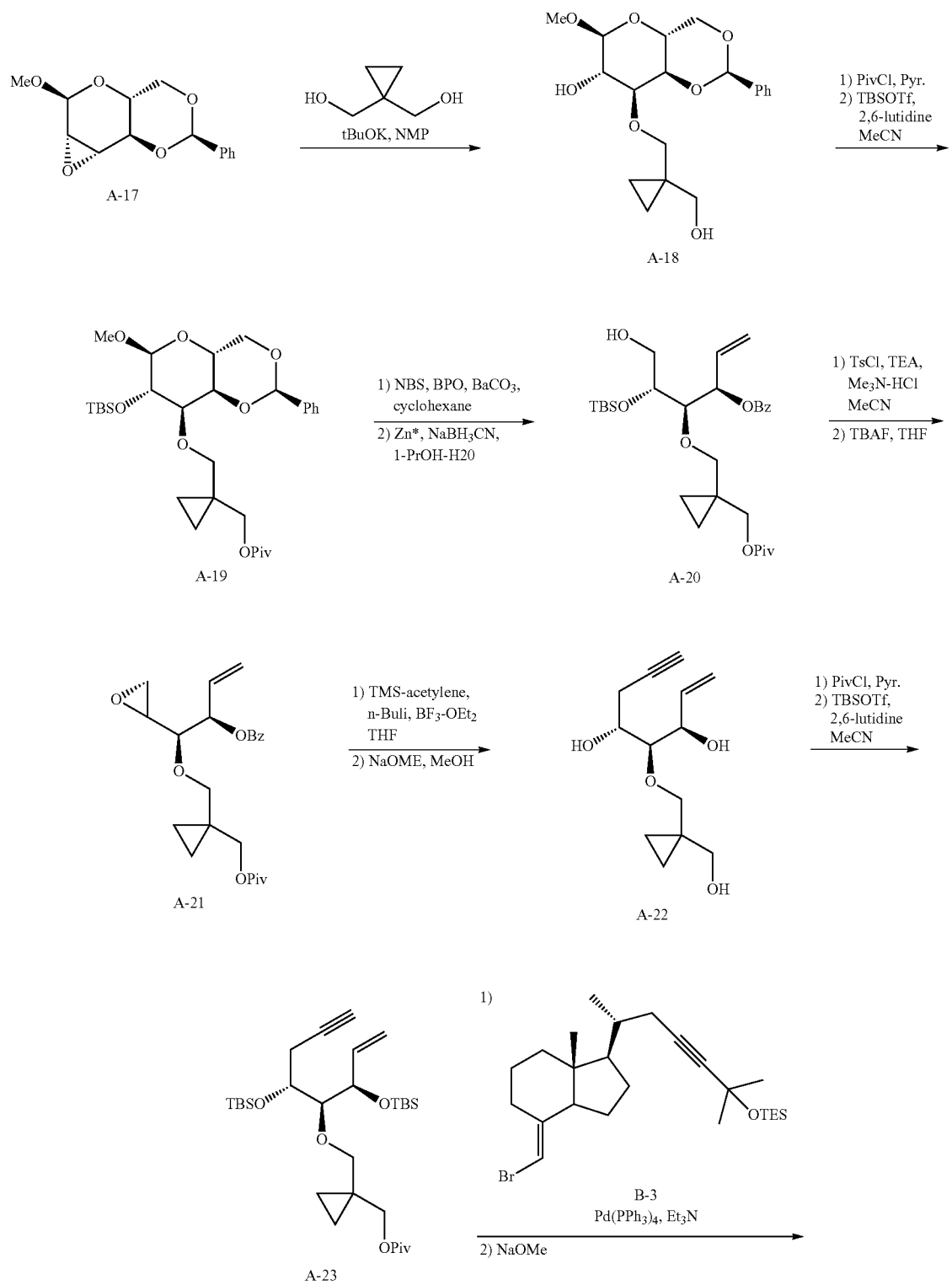

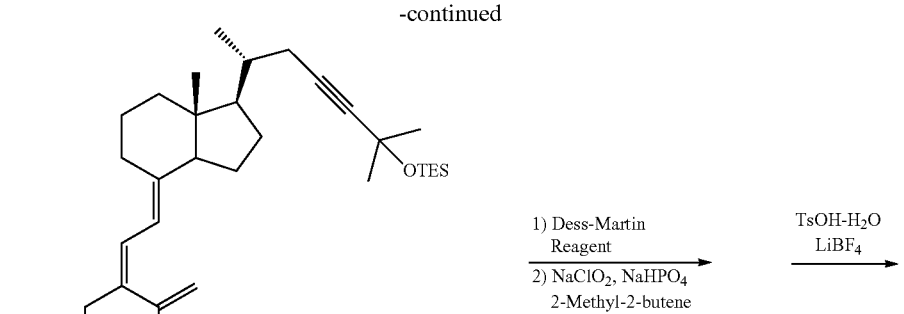

AB-3

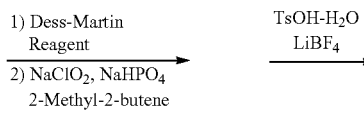

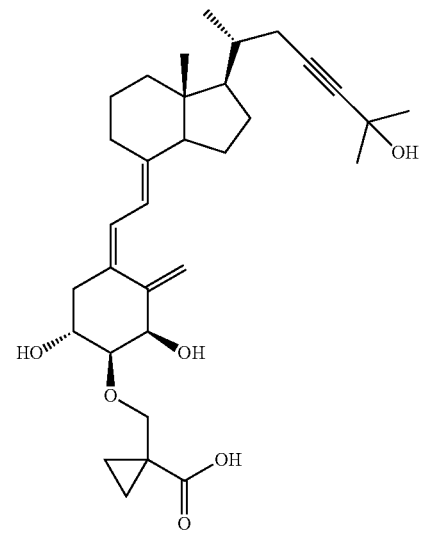

E-1

(1) The compound A-17 (6.03 g, 22.8 mmol), described in the literature (for example, Kittaka et al., J. Org. Chem., 69, 7463-7471 (2004)), was dissolved in N-methylpyrrolidone (60 mL), thereto was added potassium t-butoxide (11.88 g, 114 mmol), and the mixture was stirred under heating at 130° C. for 4 hours. The reaction mixture was cooled to room temperature, water (240 mL) and then DIAION HP-20SS (produced by Mitsubishi Chemical Corporation, 30 g (dry weight)) were added thereto, and the mixture was stirred at room temperature overnight. The reaction mixture was filtered, the solid material was washed with saturated aqueous ammonium chloride (100 mL) and water (200 mL), and extracted with acetone (500 mL). The extraction solution was concentrated under reduced pressure and diluted with ethyl acetate. The mixture was washed with saturated aqueous sodium chloride and the organic layer was dried over anhydrous magnesium sulfate. The organic layer was concentrated under reduced pressure and the residue obtained was purified by silica gel column chromatography (n-hexane/ethyl acetate=1/4) to obtain compound A-18 (1.78 g, yield 21%).

$^1$H NMR (CDCl$_3$) δ: 7.51-7.36 (5H, m), 5.54 (1H, s), 4.61 (1H, s), 4.40-4.29 (2H, m), 4.08 (1H, t, J=4.27 Hz), 4.01 (1H, dd, J=9.27, 2.68 Hz), 3.93 (1H, br s), 3.83-3.75 (3H, m), 3.60-3.50 (3H, m), 3.41 (3H, s), 0.59-0.41 (3H, m).

(2) The compound A-18 (2.97 g, 8.10 mmol) obtained in (1) was dissolved in anhydrous pyridine (30 mL) and the solution was cooled to 0° C. Thereto was added pivaloyl chloride (1.15 mL, 9.32 mmol) and the mixture was stirred at the same temperature for 1 hour. Anhydrous methanol (3 mL) was added thereto, and the mixture was stirred at room temperature for 5 minutes and concentrated under reduced pressure. The residue was dissolved in toluene, the solution was washed with saturated aqueous sodium chloride, and, thereafter, the organic layer was dried over anhydrous magnesium sulfate. The organic layer was concentrated under reduced pressure and dried. This crude material was dissolved in anhydrous dichloromethane (20 mL), the solution was cooled to 0° C., and after the addition of 2,6-lutidine (1.3 mL, 11.6 mmol) and t-butyldimethylsilyl trifluoromethanesulfonate (2.14 mL, 9.32 mmol) thereto, the mixture was stirred at room temperature for 1 hour. Anhydrous methanol (5 mL) was added and the mixture was concentrated under reduced pressure. The residue was dissolved in toluene, the solution was washed with water, and the organic layer was dried over anhydrous sodium sulfate. The solution was concentrated under reduced pressure and the residue obtained was purified by silica gel column chromatography (5% ethyl acetate/n-hexane→10% ethyl acetate/n-hexane) to obtain compound A-19 (3.19 g, yield 69%).

$^1$H NMR (CDCl$_3$) δ: 7.49-7.34 (5H, m), 5.56 (1H, s), 4.45 (1H, s), 4.29-4.25 (2H, m), 4.18 (1H, d, J=11.22 Hz), 3.98-3.92 (3H, m), 3.75 (1H, t, J=12.08 Hz), 3.65 (1H, t, J=2.68 Hz), 3.56 (2H, dd, J=29.76, 9.51 Hz), 3.35 (3H, s), 1.19 (9H, s), 0.91 (9H, s), 0.61-0.51 (4H, m), 0.10 (3H, s), 0.10 (3H, s).

(3) The compound A-19 (3.17 g, 5.61 mmol) obtained in (2) was dissolved in cyclohexane (63 mL), thereto were added barium carbonate (775 mg, 3.92 mmol), benzoyl peroxide (136 mg, 0.56 mmol), and N-bromosuccinimide (1.21 g, 6.73 mmol), and the mixture was heated under reflux for 1 hour. After cooling, the mixture was filtered through celite, and the organic layer was washed in the order of saturated aqueous sodium hydrogen carbonate and saturated aqueous sodium chloride. Thereafter, the organic layer was dried over anhydrous magnesium sulfate and concentrated under reduced pressure to obtain a crude material (4.0 g). This crude material was dissolved in a mixed solvent of 1-propanol (36 mL) and water (4 mL), thereto were added activated zinc (7.38 g, 112.2 mmol) and sodium cyanoborohydride (1.42 g, 22.4 mmol), and the mixture was heated under reflux for 1 hour. After cooling, the mixture was filtered through celite, the solid was washed with 1-propanol, and thereafter the liquid was concentrated under reduced pressure. The residue obtained was diluted with ethyl acetate, washed with saturated aqueous sodium chloride, and the organic layer was dried over anhydrous magnesium sulfate. The organic layer was concentrated under reduced pressure and the residue obtained was purified by silica gel column chromatography (hexane/ethyl acetate=90/10→80/20) to obtain compound A-20 (1.50 g, yield 50%).

$^1$H NMR (CDCl$_3$) δ: 8.05-8.02 (2H, m), 7.59-7.43 (3H, m), 6.11 (1H, ddd, J=11.00, 17.32, 6.00 Hz), 5.78-5.75 (1H, m), 5.41 (1H, dt, J=17.32, 1.34 Hz), 5.30 (1H, dt, J=10.49, 1.22 Hz), 4.17 (1H, d, J=11.47 Hz), 3.96-3.93 (2H, m), 3.81 (1H, dd, J=11.47, 5.12 Hz), 3.73-3.68 (2H, m), 3.64 (1H, d, J=9.76 Hz), 3.50 (1H, d, J=9.76 Hz), 1.18 (9H, s), 0.90 (9H, s), 0.55 (4H, t, J=1.95 Hz), 0.09 (3H, s), 0.07 (3H, s).

(4) The compound A-20 (2.41 g, 4.5 mmol) obtained in (3) was dissolved in acetonitrile (25 mL), thereto were added triethylamine (1.26 mL, 9 mmol), trimethylamine hydrochloride (86 mg, 0.9 mmol), and p-toluenesulfonyl chloride (1.30 g, 6.8 mmol) in this order, and the mixture was stirred at room temperature for 1 hour. Saturated aqueous sodium hydrogen carbonate was added thereto and the mixture was concentrated under reduced pressure. The residue was diluted with ethyl acetate and the mixture was washed with saturated aqueous sodium chloride. The organic layer was dried over anhydrous magnesium sulfate and concentrated under reduced pressure. The crude material (3.31 g) was dissolved in tetrahydrofuran (18 mL), thereto was added tetrabutylammonium fluoride (1 M tetrahydrofuran solution, 13.5 mL, 13.5 mmol), and the mixture was heated under reflux for 1.5 hours. After cooling, the mixture was concentrated under reduced pressure and the residue was diluted with toluene. The mixture was washed with saturated aqueous sodium chloride, and the organic layer was dried over anhydrous magnesium sulfate and concentrated under reduced pressure. The residue obtained was purified by silica gel column chromatography (hexane/ethyl acetate=90/10) to obtain compound A-21 (851 mg, yield 47%).

$^1$H NMR (CDCl$_3$) δ: 8.06-8.02 (2H, m), 7.61-7.44 (3H, m), 6.10-6.01 (1H, m), 5.67-5.64 (1H, m), 5.42 (1H, dt, J=17.24, 1.34 Hz), 5.32 (1H, dt, J=10.57, 1.22 Hz), 4.04 (2H, dd, J=27.32, 11.22 Hz), 3.65 (1H, d, J=10.24 Hz), 3.53 (1H, d, J=10.24 Hz), 3.17 (1H, dd, J=7.32, 5.37 Hz), 3.10-3.06 (1H, m), 2.75 (1H, t, J=4.39 Hz), 2.60 (1H, dd, J=4.88, 2.93 Hz), 1.19 (9H, s), 0.55 (4H, s).

(5) A tetrahydrofuran solution (3 mL) of trimethylsilylacetylene (1.62 mL, 11.5 mmol) was placed under a nitrogen atmosphere and the solution was cooled with dry ice-acetone. Hereto was added a hexane solution of n-butyllithium (2.64 M, 3.97 mL, 10.5 mmol) and the mixture was stirred for 45 minutes. To this mixture were added a tetrahydrofuran solution (6 mL) of the compound A-21 (846 mg, 2.1 mmol) obtained in (4) and trifluoroborane-diethyl ether complex (0.343 mL, 2.73 mmol), and the mixture was stirred for 2 hours under dry ice-acetone cooling and further stirred for 1 hour at 0° C. Saturated aqueous ammonium chloride was added thereto, and the mixture was returned to room temperature and diluted with ethyl acetate. The solution was washed successively with saturated aqueous sodium hydrogen carbonate and saturated aqueous sodium chloride, and the organic layer was dried over anhydrous magnesium sulfate and concentrated under reduced pressure. The residue obtained was dissolved in anhydrous methanol (10 mL), sodium methoxide (870 mg, 6.3 mmol) was added thereto, and the mixture was stirred under heating at 50° C. for 1 hour. After cooling, the mixture was concentrated under reduced pressure. The residue was diluted with ethyl acetate, thereafter the mixture was washed with saturated aqueous sodium chloride, and the organic layer was dried over anhydrous magnesium sulfate. The organic layer was concentrated under reduced pressure and the residue obtained was purified by silica gel column chromatography (hexane/ethyl acetate=60/40→50/50→35/65) to obtain Compound A-22 (311.5 mg, yield 62%).

$^1$H NMR (CDCl$_3$) δ: 5.57 (1H, ddd, J=17.00, 11.00, 6.00 Hz), 4.88 (1H, dt, J=17.00, 1.70 Hz), 4.73 (1H, dt, J=11.00, 1.70 Hz), 3.85-3.81 (1H, m), 3.51 (1H, ddd, J=8.42, 5.73, 2.07 Hz), 3.16 (1H, d, J=9.50 Hz), 3.05 (1H, d, J=9.50 Hz), 2.85 (2H, dd, J=4.63, 2.20 Hz), 2.12-1.92 (2H, m), 1.85 (1H, t, J=2.68 Hz).

(6) The compound A-22 (534.4 mg, 2.26 mmol) obtained in (5) was dissolved in anhydrous pyridine (7.5 mL) and, after the addition of pivaloyl chloride (0.276 mL, 2.26 mmol) at 0° C., the mixture was stirred at the same temperature for 45 minutes. Saturated aqueous sodium hydrogen carbonate was added to the mixture. The mixture was diluted with toluene and washed with brine. The organic layer was dried over anhydrous magnesium sulfate and evaporated to give the residue. The residue was diluted with dry dichloromethane (10 mL), and to the solution were added 2,6-lutidine (1.1 mL, 9.22 mmol) and t-butyldimethylsilyl trifluoromethanesulfonate (1.7 mL, 7.55 mmol) at 0° C. The reaction mixture was stirred at same temperature for 1.5 hours. The reaction was diluted with ethyl acetate and the organic layer was washed with brine, dried over anhydrous magnesium sulfate and evaporated. The residue was purified by silica gel column chromatography (hexane/ethyl acetate=99/1→85/15) to obtain A-23 (1.08 g, yield 91%).

$^1$H-NMR (CDCl$_3$) δ: 6.00-5.91 (1H, m), 5.21 (1H, d, J=17.32 Hz), 5.13 (1H, d, J=11.00 Hz), 4.32 (1H, dd, J=7.07, 3.90 Hz), 4.03 (2H, dd, J=19.03, 11.22 Hz), 3.94 (1H, dd, J=10.73, 5.85 Hz), 3.64 (1H, d, J=9.76 Hz), 3.45 (1H, d, J=9.76 Hz), 3.39 (1H, t, J=4.27 Hz), 2.51 (1H, ddd, J=16.83, 6.00, 3.00 Hz), 2.36 (1H, ddd, J=16.71, 6.10, 2.56 Hz), 1.95

(1H, t, J=2.56 Hz), 1.19 (9H, s), 0.90 (9H, s), 0.88 (9H, s), 0.55-0.48 3H, m), 0.11 (3H, s), 0.09 (3H, s), 0.06 (3H, s), 0.03 (3H, s).

(7) Using the compound A-23 (70 mg, 0.15 mmol) obtained in (6) and the compound B-3 (69 mg, 0.16 mmol) obtained in Example 1 (4) as starting materials, synthesis was carried out in the same manner as in Example 1 (5) to obtain compound AB-3 (48.1 mg, 37.4%).

¹H-NMR (CDCl₃) δ: 6.18 (1H, d, J=10.98 Hz), 6.02 (1H, d, J=11.47 Hz), 5.32 (1H, s), 5.01 (1H, s), 4.47 (1H, s), 4.03 (1H, q, J=4.15 Hz), 3.91 (1H, d, J=9.03 Hz), 3.58 (1H, dd, J=11.10, 4.03 Hz), 3.46-3.39 (2H, m), 3.32 (1H, d, J=9.51 Hz), 3.21 (1H, br s), 2.80 (1H, t, J=7.81 Hz), 2.61 (1H, d, J=13.42 Hz), 2.24 (1H, dd, J=16.34, 3.42 Hz), 2.10 (1H, dd, J=13.66, 4.15 Hz), 2.05-1.84 (4H, m), 1.66-1.49 (12H, m), 1.43-1.30 (4H, m), 1.07 (4H, d, J=6.59 Hz), 0.98-0.83 (36H, m), 0.82-0.81 (2H, m), 0.70-0.64 (9H, m), 0.57-0.54 (6H, m), 0.51-0.36 (6H, m), 0.11 (3H, s), 0.10 (3H, s), 0.08 (3H, s), 0.07 (3H, s).

(8) Using the compound AB-3 (48.1 mg, 0.056 mmol) obtained in (7) as a raw material, treatments were carried out in the same manner as in Example 1 (6). The reaction product (28.5 mg, 0.0327 mmol) was dissolved in a mixed solvent of anhydrous dichloromethane/acetonitrile (1/1, 1 mL) and the solution was cooled to 0° C. Thereafter, tosylic acid monohydrate (31 mg, 0.163 mmol) and lithium tetrafluoroborate (30 mg, 0.327 mmol) were added, and the mixture was stirred at the same temperature for 30 minutes. To the reaction mixture was added saturated aqueous sodium hydrogen carbonate and the mixture was extracted with ethyl acetate. The organic layer was dried over anhydrous magnesium sulfate and concentrated under reduced pressure. The residue obtained was roughly purified by thin-layer silica gel chromatography (ethyl acetate/acetone=9/1+0.5% acetic acid) and further purified by reversed-phase HPLC (A=95% water/acetonitrile; B=0.5% water/40% methanol/acetonitrile; B=85%) to obtain compound E-1 (4.9 mg, yield 16.6%).

¹H-NMR (CDCl₃) δ: 6.41 (1H, d, J=11.22 Hz), 6.01 (1H, d, J=10.98 Hz), 5.37 (1H, s), 5.08 (1H, d, J=1.46 Hz), 4.48 (1H, d, J=2.68 Hz), 4.06-3.82 (2H, m), 3.55-3.25 (2H, m), 2.88-2.60 (2H, m), 2.28-1.54 (13H, m), 1.42-1.20 (10H, m), 1.10-1.08 (1H, m), 1.06 (3H, d, J=6.59 Hz), 0.91 (3H, d, J=4.88 Hz), 0.54 (3H, s).

Example 10

Production of (5Z,7E)-(1R,2S,3R,20R)-2-(2-carboxyethoxy)-26,27-dimethyl-23-yne-9,10-seco-5,7,10(19)-cholestatriene-1,3,25-triol (Compound F-1)

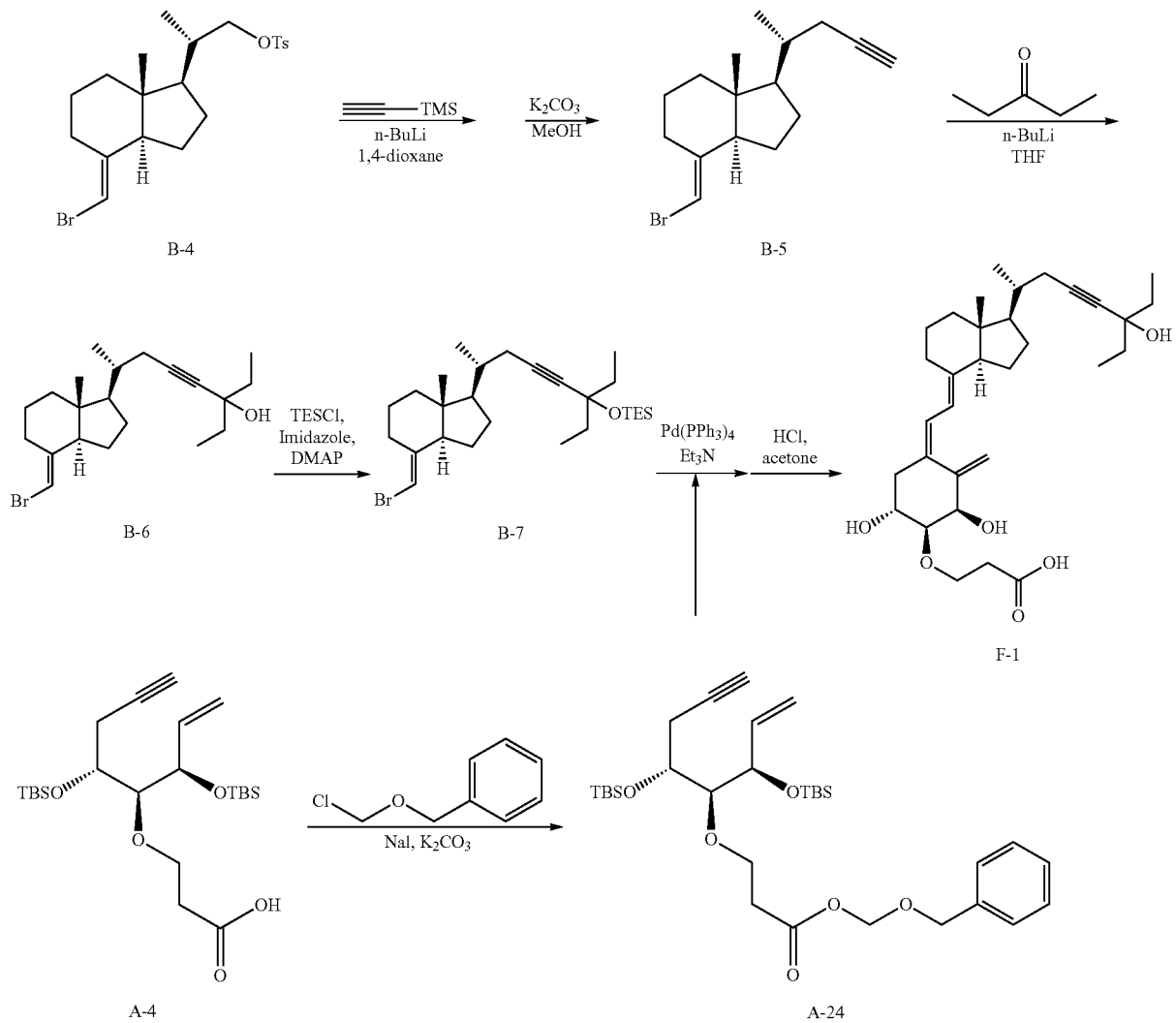

(1) Trimethylsilylacetylene (1.84 mL, 13.0 mmol) was dissolved in 1,4-dioxane (15 mL) and, under an argon atmosphere and ice-bath cooling, thereto was added dropwise n-butyllithium (1.59 M n-hexane solution, 8.18 mL, 13.0 mmol) over 10 minutes. Hereto was added compound B-4 (1.91 g, 4.33 mmol) dissolved in 1,4-dioxane (10 mL), the compound B-4 being synthesized according to the method of Tanaka et al. (International Publication No. WO 98/58909), and the mixture was heated under reflux at 110° C. for 24 hours. After cooling to room temperature, saturated aqueous ammonium chloride was added to the mixture, followed by stirring. Thereafter, the mixture was extracted with n-hexane, and the organic layer obtained was washed with saturated aqueous sodium chloride, dried over anhydrous sodium sulfate, and concentrated under reduced pressure. The residue obtained was dissolved in tetrahydrofuran-methanol (1:1, 20 mL), potassium carbonate (718 mg, 5.20 mmol) was added thereto, and the mixture was stirred at room temperature overnight. Water was added to the reaction mixture and, thereafter, the mixture was extracted with n-hexane. The organic layer obtained was washed with saturated sodium chloride and dried over anhydrous sodium sulfate. The organic layer was concentrated under reduced pressure and the residue obtained was purified by silica gel column chromatography (n-hexane) to obtain compound B-5 (1.14 g, yield 89%).

$^1$H-NMR (CDCl$_3$) δ: 5.65 (1H, s), 2.90-2.86 (1H, m), 2.25 (1H, dt, J=16.6, 3.0 Hz), 2.10-1.88 (5H, m), 1.72-1.25 (9H, m), 1.11 (3H, d, J=6.6 Hz), 0.58 (3H, s).

(2) The compound B-5 (301 mg, 1.02 mmol) obtained in (1) was dissolved in tetrahydrofuran (10 mL) and, under an argon atmosphere and cooling to −78° C., n-butyllithium (1.59 M n-hexane solution, 0.673 mL, 1.02 mmol) was added dropwise thereto, and the mixture was stirred for 30 minutes. Hereto was added 3-pentanone (0.216 mL, 2.04 mmol) and the mixture was stirred for 1 hour with the temperature maintained at −78° C. To the reaction mixture was added saturated aqueous ammonium chloride and the mixture was warmed to room temperature. The reaction mixture was extracted with ethyl acetate, and the organic layer obtained was washed with saturated aqueous sodium chloride and dried over anhydrous sodium sulfate. The organic layer was concentrated under reduced pressure and the residue obtained was purified by silica gel column chromatography (n-hexane/ethyl acetate=9/1) to obtain compound B-6 (205 mg, yield 53%).

$^1$H-NMR (CDCl$_3$) δ: 6.42 (1H, d, J=11.2 Hz), 6.02 (1H, d, J=11.2 Hz), 5.39 (1H, s), 5.10 (1H, s), 4.44 (1H, t, J=3.9 Hz), 4.11-4.07 (1H, m), 3.84-3.81 (1H, m), 3.75-3.68 (2H, m), 3.39 (1H, dd, J=7.4, 3.3 Hz), 2.84-2.81 (1H, m), 2.68 (1H, dd, J=13.7, 4.4 Hz), 2.52 (2H, t, J=6.8 Hz), 2.29-2.20 (3H, m), 2.15-1.83 (6H, m), 1.70-1.22 (14H, m), 1.08-1.01 (9H, m), 0.55 (3H, s) ppm.

(3) The compound B-6 (396 mg, 1.04 mmol) obtained in (2) was dissolved in anhydrous N,N-dimethylformamide (4 mL), thereto were added chlorotriethylsilane (0.283 mL, 1.68 mmol), imidazole (152 mg, 2.23 mmol), and 4-dimethylaminopyridine (27 mg, 0.22 mmol), and the mixture was stirred under heating at 50° C. for 1 hour. The reaction mixture was cooled to room temperature, anhydrous methanol (1 mL) was added thereto, and the mixture was stirred for 30 minutes. The mixture was diluted with toluene and washed with saturated aqueous sodium chloride. Thereafter, the organic layer was dried over anhydrous magnesium sulfate and concentrated under reduced pressure. The residue obtained was purified by silica gel column chromatography (n-hexane/ethyl acetate=90/10) to obtain compound B-7 (454.8 mg, yield 88%).

$^1$H-NMR (CDCl$_3$) δ: 5.65 (1H, s), 2.91-2.85 (1H, m), 2.24 (1H, dd, J=16.46, 3.54 Hz), 2.10 (1H, dd, J=16.58, 6.83 Hz), 2.02-1.88 (4H, m), 1.71-1.58 (9H, m), 1.54-1.24 (7H, m), 1.08 (3H, d, J=8.00 Hz), 0.98-0.91 (22H, m), 0.73-0.64 (9H, m), 0.58 (3H, s), 0.52 (2H, q, J=7.97 Hz).

(4) The compound A-4 (457 mg, 1 mmol) obtained in Example 2 (1) was dissolved in anhydrous N,N-dimethylformamide (5 mL), thereto were added triethylamine (0.421 mL, 3 mmol) and chloromethyl benzyl ether (0.276 mL, 2 mmol), and the mixture was stirred at 0° C. for 1 hour 45 minutes Saturated aqueous sodium hydrogen carbonate was added thereto and the mixture was extracted with ethyl acetate. The organic layer was washed with saturated aqueous sodium chloride, dried over anhydrous magnesium sulfate, and, thereafter, concentrated under reduced pressure. The residue obtained was purified by silica gel column chromatography (n-hexane/ethyl acetate=95/5) to obtain compound A-24 (485 mg, yield 84%).

(5) Using the compound B-7 (44 mg, 0.09 mmol) obtained in (3) and the compound A-24 (43 mg, 0.075 mmol) obtained in (4) as raw materials, the coupling reaction and the deprotection reaction were carried out in the same manner as in Example 5 (4). The crude reaction product obtained was roughly purified by thin-layer silica gel chromatography (ethyl acetate/acetone=4/1+acetic acid (1.5 v/v %)) and further purified by reversed-phase HPLC (A=95% water/acetonitrile; B=0.5% water/40% methanol/acetonitrile; B=75%) to obtain compound F-1 (4.7 mg, yield 12%).

$^1$H-NMR (CDCl$_3$) δ: 6.42 (1H, d, J=10.98 Hz), 6.00 (1H, d, J=10.98 Hz), 5.37 (1H, d, J=1.46 Hz), 5.08 (1H, d, J=1.95 Hz), 4.47 (1H, d, J=2.93 Hz), 4.08-3.94 (2H, m), 3.82-3.74 (1H, m), 3.33 (1H, dd, J=8.17, 3.05 Hz), 2.83 (1H, d, J=12.20 Hz), 2.69-2.60 (3H, m), 2.30-2.20 (2H, m), 1.98 (2H, d, J=11.71 Hz), 1.91-1.80 (1H, m), 1.72-1.24 (16H, m), 1.07 (3H, d, J=6.34 Hz), 1.03 (8H, t, J=7.44 Hz), 0.54 (3H, s).

Example 11

Production of (5Z,7E)-(1R,2S,3R,20R)-2-(2-carboxyethoxy)-26,27-nor-25-cyclopentyl-23-yne-9,10-seco-5,7,10(19)-cholestatriene-1,3,25-triol (Compound F-2)

Formula 19

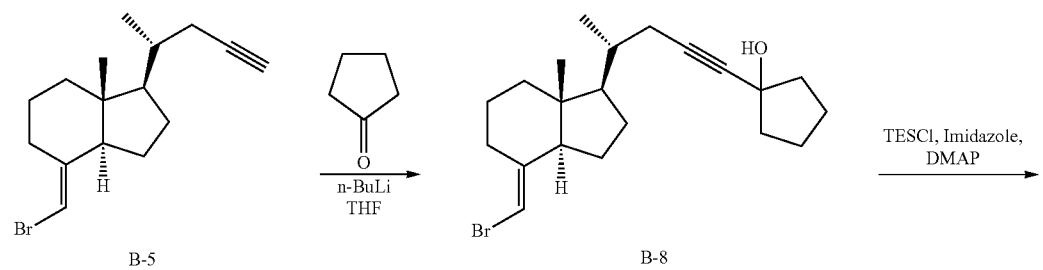

-continued

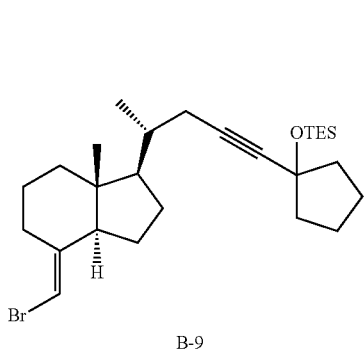
B-9

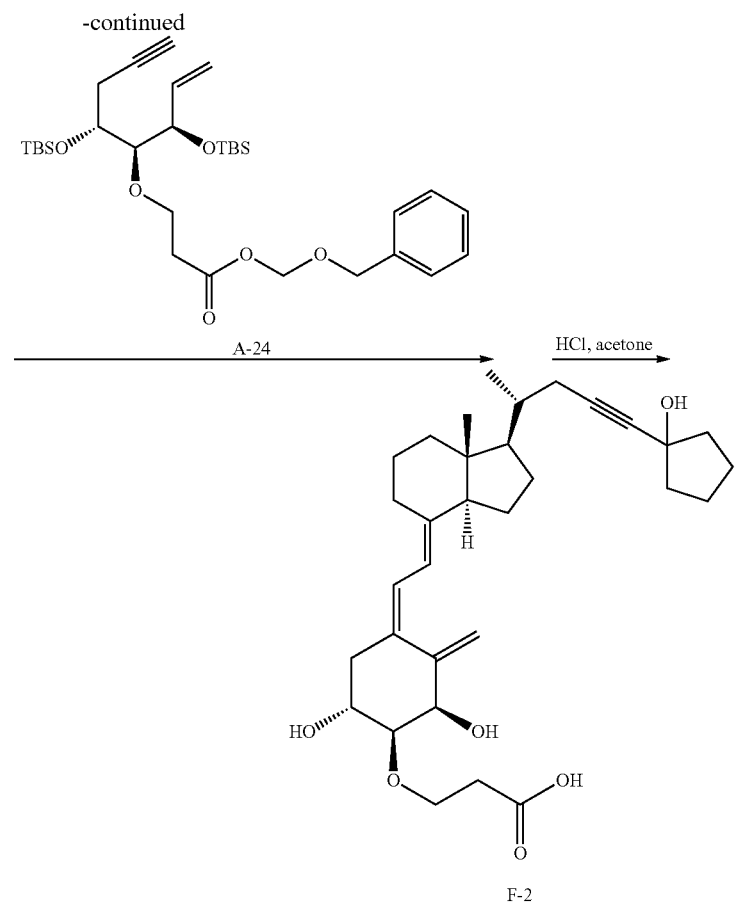

(1) Using the compound B-5 (442 mg, 1.5 mmol) obtained in Example 10 (1) as a starting material, synthesis was carried out in the same manner as in Example 10 (2) to obtain a mixture (427.2 mg) of compound B-8 and cyclopentanone. Using this crude material as a starting material and using anhydrous N,N-dimethylformamide (4.5 mL), chlorotriethylsilane (0.283 mL, 1.68 mmol), imidazole (152 mg, 2.23 mmol), and 4-dimethylaminopyridine (27 mg, 0.22 mmol), synthesis was carried out in the same manner as in Example 10 (3) to obtain compound B-9 (506.2 mg, yield 68%).

$^1$H-NMR (CDCl$_3$) δ: 5.65 (1H, s), 2.92-2.85 (1H, m), 2.24 (1H, dd, J=16.46, 3.29 Hz), 2.08 (1H, dd, J=16.10, 6.83 Hz), 2.02-1.57 (19H, m), 1.54-1.26 (7H, m), 1.07 (4H, d, J=7.56 Hz), 0.98-0.91 (15H, m), 0.73-0.63 (8H, m), 0.57 (3H, s), 0.52 (3H, q, J=7.97 Hz).

(2) Using the compound B-9 (44 mg, 0.09 mmol) obtained in (1) and the compound A-24 (43 mg, 0.075 mmol) obtained in Example 10 (4) as starting materials, synthesis was carried out in the same manner as in Example 10 (5) to obtain compound F-2 (2.0 mg, yield 5%).

$^1$H-NMR (CDCl$_3$) δ: 6.41 (1H, d, J=10.98 Hz), 6.00 (1H, d, J=10.98 Hz), 5.36 (1H, s), 5.07 (1H, s), 4.46 (1H, s), 4.10-3.93 (2H, m), 3.78 (1H, br s), 3.30 (1H, d, J=6.59 Hz), 3.07-2.62 (9H, m), 2.30-2.19 (2H, m), 2.05-1.24 (25H, m), 1.06 (3H, d, J=6.59 Hz), 0.54 (3H, s).

Example 12

Evaluation of VDR affinity

VDR was evaluated by using a commercial measurement and evaluation kit, for example, "PolarScreen Vitamin D Receptor Competitor Assay, Red, Cat. No. PV4569" marketed by Invitrogen Corporation, according to the following procedure.

Solutions of the compounds were added to two wells each of a 384-well black plate in 10 μl aliquots. To each well, VDR/Fluoromone VDR Complex included in the kit was added in 10 μl aliquots and allowed to react at room temperature for 2 hours. After 2 hours, fluorescence polarization was measured and VDR affinity was evaluated. In addition, the affinity was evaluated in relative values (1/X) with the affinity of 1,25-(OH)2-vitamin D$_3$ taken as 1.

TABLE 2

| Compound Name | VDR Affinity (1/X) |
| --- | --- |
| 1,25-(OH)2-Vitamin D$_3$ | 1/1 |
| Compound C-1 | 1/0.52 |
| Compound D-1 | 1/0.92 |
| Compound E-1 | 1/2.39 |
| Compound F-1 | 1/1.23 |
| Compound F-2 | 1/1.61 |

The compounds obtained according to the present invention were confirmed to have strong VDR affinity. Especially, Compound C-1 and Compound D-1 were found to have very strong VDR affinity.

Example 13

VDR Transcriptional Activity in Human Osteoblast (HOS Cells)

(1) A reporter vector was constructed by inserting the sequence of the promoter region of human ostocalcin gene into the upstream of luciferase gene using a pGL3 vector (Promega Corporation), wherein the promoter region of the human ostocalcin gene was cloned using cDNA acquired from HOS cells (purchased from ATCC) by a method known in the literature (Ozono et al., The Journal of Biological Chemistry, 265, 21881-21888 (1990)). The expression vector was constructed by inserting a DNA sequence, which encodes human VDR and human RXR, into a pcDNA3 vector (Invitrogen Corporation). The HOS cells were incubated in a DMEM medium containing 10% FBS under conditions of 37° C. and 5% $CO_2$, and subcultured every 2 or 3 days.

(2) The cells which had been subcultured were recovered by centrifugation and were suspended in serum- and phenol red-free DMEM medium in a density of $4 \times 10^5$ cells/mL. This was seeded on a 96-well plate in an amount of 0.1 mL/well. To this system, various vectors described in (1) were added in an amount of 0.05 mL per well using Lipofectamine 2000 (Invitrogen Corporation). After incubation at 37° C. for 3 hours, 2 µl each of ethanol solutions of the test compounds of various concentrations or ethanol as a control was added to each well. After incubation at 37° C. for 24 hours, the medium was removed, the cells were washed once with PBS(−), and thereafter luciferase activity was measured by using a luminometer (Berthold Technologies GmbH & Co. KG) using Dual-Glo Luciferase Assay Kit (Promega Corporation).

As a result, all of the compounds of the present invention were found to have transcriptional activity with $EC_{50}$ values of 20 nM or less. Further, Compounds C-1, C-2, D-1, E-1, F-1, and F-2 were found to possess transcriptional activity with $EC_{50}$ values of 0.2 nM or less. Especially, D-1, F-1, and F-2 were found to have transcriptional activity with $EC_{50}$ values of 0.02 nM or less.

Example 14

Bone Mineral Density-Enhancing Effect in Osteoporosis Model (Oophorectomy) Rats (Comparative Test)

Twelve-week old SD stock female rats (Charles River Japan, Inc.) were subjected to bilateral oophorectomy and, after being left alone for 4 weeks, the compounds of the present invention and 2α-(3-hydroxypropyl)oxy-1α,25-dihydroxyvitamin $D_3$ described in International Publication No. WO 01/62723 were each administered 5 times a week for 4 weeks. After 24 hours from the final administration, blood was drawn under ether anesthesia and the rats were put down. Under anesthesia, bone mineral density of the fourth and fifth lumbar vertebrae was measured by using a dual-energy X-ray bone mineral analyzer (QDR-2000; Hologic, Inc.). For comparison, a sham surgery (sham) group (abdominal operation is performed but the ovary is not removed; the test compounds are not administered) and an oophorectomy (OVX) group (subjected to oophorectomy but the test compounds are not administered) were also subjected to measurement of the bone mineral density of lumbar vertebrae at the time of dissection. Further, measurement of calcium concentration in the serum of each group was also performed.

TABLE 3

| Group | Dose (ng/kg) | Bone mineral density (g/cm³) | Serum calcium value (mg/dL) |
|---|---|---|---|
| Test 1 | | | |
| Sham | — | 0.2303 ± 0.0185 | 9.61 ± 0.16 |
| OVX | — | 0.2048 ± 0.0139 | 9.64 ± 0.22 |
| Compound C-1 | 4 | 0.2223 ± 0.0118 | 10.40 ± 1.00 |
|  | 10 | 0.2400 ± 0.0065 | 10.30 ± 0.20 |
| Test 2 | | | |
| Sham | — | 0.2242 ± 0.0121 | 10.14 ± 0.17 |
| OVX | — | 0.2152 ± 0.0166 | 9.73 ± 0.15 |
| Compound C-2 | 6 | 0.2196 ± 0.0177 | 9.83 ± 0.37 |
|  | 13 | 0.2308 ± 0.0081 | 10.19 ± 0.36 |
| Test 3 | | | |
| Sham | — | 0.2338 ± 0.0120 | 9.71 ± 0.27 |
| OVX | — | 0.2194 ± 0.0100 | 9.25 ± 0.11 |
| Compound C-5 | 17 | 0.2316 ± 0.0134 | 9.60 ± 0.15 |
|  | 50 | 0.2354 ± 0.0126 | 10.10 ± 0.21 |
| Test 4 | | | |
| Sham | — | 0.2422 ± 0.0130 | 10.01 ± 0.04 |
| OVX | — | 0.2163 ± 0.0100 | 9.58 ± 0.18 |
| Compound C-7 | 6 | 0.2322 ± 0.0092 | 9.83 ± 0.22 |
|  | 13 | 0.2548 ± 0.0143 | 10.07 ± 0.22 |
| Test 5 | | | |
| Sham | — | 0.2252 ± 0.0080 | 9.82 ± 0.22 |
| OVX | — | 0.2115 ± 0.0110 | 9.53 ± 0.28 |
| Compound D-1 | 6 | 0.2211 ± 0.0175 | 9.75 ± 0.10 |
|  | 13 | 0.2360 ± 0.0143 | 10.23 ± 0.26 |
| Test 6 | | | |
| Sham | — | 0.2302 ± 0.0110 | 9.61 ± 0.16 |
| OVX | — | 0.2042 ± 0.0070 | 9.64 ± 0.22 |
| Compound D-6 | 50 | 0.2365 ± 0.0204 | 9.76 ± 0.29 |

TABLE 4

| Group | Dose (ng/kg) | Bone mineral density (g/cm³) | Serum calcium value (mg/dL) |
|---|---|---|---|
| Test 7 | | | |
| Sham | — | 0.2252 ± 0.0080 | 9.82 ± 0.22 |
| OVX | — | 0.2115 ± 0.0110 | 9.53 ± 0.28 |
| Compound F-1 | 6 | 0.2366 ± 0.0139 | 10.12 ± 0.59 |
| Comparative Test | | | |
| Sham | — | 0.2451 ± 0.0251 | 10.50 ± 0.83 |
| OVX | — | 0.2167 ± 0.0126 | 9.60 ± 0.23 |
| 2α-(3-hydroxypropyl)oxy-1α,25-dihydroxy-vitamin $D_3$ | 10 | 0.2269 ± 0.0161 | 10.30 ± 0.37 |
|  | 25 | 0.2473 ± 0.0157 | 11.20 ± 0.20 |

The bone mineral density of the OVX group was confirmed to decrease compared to the sham surgery (sham) group by performing the operation. Also, the bone mineral density was confirmed to recover by administration of vitamin D derivatives. However, the group which was administered with 2α-(3-hydroxypropyl)oxy-1α,25-dihydroxyvitamin $D_3$ described in International Publication No. WO 01/62723 showed increase in the serum calcium value with increase in the bone mineral density and, at a dose (25 ng/kg) necessary for the bone mineral density to become equal to or greater than the sham group, the serum calcium value was found to increase significantly, by 1 mg/dL or more. On the other hand, the compounds of the present invention were found to enhance bone mineral density to a value equivalent to or greater than that of the sham group, while the increase in the serum calcium value compared to that of the OVX group was found in a range of not more than 1 mg/dL.

From the results described above, the vitamin $D_3$ derivatives or medicinally acceptable solvates thereof of the present invention were found to have more excellent effects on bones than the heretofore reported vitamin $D_3$ derivatives.

The vitamin $D_3$ derivatives or medicinally acceptable solvates thereof of the present invention can be used as drugs.

The invention claimed is:

1. A compound represented by the following formula (1):

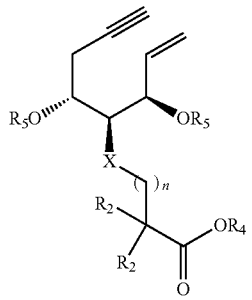

(1)

wherein $R_2$ represents a hydrogen atom or an alkyl group having 1 to 6 carbon atoms or, together with the other $R_2$ and the carbon atom to which they are bound to, may form a cyclic alkyl group having 3 to 6 carbon atoms;

$R_4$ represents a hydrogen atom, alkyl group having 1 to 6 carbon atoms, an alkylcarbonyloxyalkyl group with each alkyl having 1 to 6 carbon atoms, an arylcarbonyloxyalkyl group with the aryl having 6 to 10 carbon atoms and the alkyl having 1 to 6 carbon atoms, a methoxymethyl group, a methoxyethoxymethyl group, a tetrahydrofuranyl group, a tetrahydropyranyl group, or a benzyloxymethyl group;

$R_5$ represents a protecting group for a hydroxyl group;

X represents an oxygen atom or a methylene group; and n represents an integer of 1 or 2.

* * * * *